US 8,484,048 B2

(12) United States Patent
Halsted et al.

(10) Patent No.: US 8,484,048 B2
(45) Date of Patent: Jul. 9, 2013

(54) AUTOMATED SYSTEM AND METHOD FOR PRIORITIZATION OF WAITING PATIENTS

(75) Inventors: Mark J. Halsted, Wyoming, OH (US);
Neil D. Johnson, Indian Hill, OH (US);
Craig M. Froehle, Cincinnati, OH (US)

(73) Assignee: Cincinnati Children's Hospital Medical Center, Cincinnati, OH (US)

( * ) Notice: Subject to any disclaimer, the term of this patent is extended or adjusted under 35 U.S.C. 154(b) by 701 days.

(21) Appl. No.: 11/603,911

(22) Filed: Nov. 22, 2006

(65) Prior Publication Data
US 2007/0226008 A1   Sep. 27, 2007

Related U.S. Application Data

(63) Continuation of application No. PCT/US2006/010660, filed on Mar. 23, 2006.

(60) Provisional application No. 60/664,517, filed on Mar. 23, 2005.

(51) Int. Cl.
*G06Q 10/00*   (2012.01)

(52) U.S. Cl.
USPC .............................................. 705/3; 235/385

(58) Field of Classification Search
USPC ............................................................. 705/3
See application file for complete search history.

(56) References Cited

U.S. PATENT DOCUMENTS

| | | |
|---|---|---|
| 5,255,187 A | 10/1993 | Sorensen |
| 5,471,382 A | 11/1995 | Tallman et al. |
| 5,622,171 A | 4/1997 | Asada et al. |
| 5,857,030 A | 1/1999 | Gaborski et al. |
| 5,964,700 A | 10/1999 | Tallman et al. |
| 5,991,730 A | 11/1999 | Lubin et al. |

(Continued)

FOREIGN PATENT DOCUMENTS
EP    0 489 209 A1   6/1992

OTHER PUBLICATIONS

PCT/US06/10660, Oct. 6, 2006, Children's Hospital Medical Center, Int'l Search Report and Written Opinion.

(Continued)

*Primary Examiner* — Hiep V Nguyen
(74) *Attorney, Agent, or Firm* — Baker & Hostetler LLP

(57) ABSTRACT

The present invention provides an automated triage system performs a computerized method that includes the steps of: (1) for plurality of patients, gathering medical factor(s) associated with each patient's medical condition, where the medical condition may be (a) a type of injury, (b) a symptom, (c) a condition of a patient, and/or (d) a demographic statistic of the patient; (2) for the same plurality of patients, gathering subjective perception(s) associated with each patient's medical condition, which may be (a) the anxiety of the patient, (b) the anxiety/concern of the referring physician, and/or (c) the anxiety of the reviewing attendee; and (3) ordering, by a computerized algorithm, the plurality of patients for medical treatment and/or medical assessment, based upon the medical factors and subjective perceptions gathered for each of the plurality of patients. The method may also include the step of gathering operational aspect(s), such as (a) waiting time of the patient, (b) medical treatment facilities availability, (c) medical treatment staff availability, (d) medical assessment facilities availability, and/or (e) medical assessment staff availability; where the ordering step includes the step of ordering, by the computer algorithm, the plurality of patients for medical treatment and/or medical assessment, based at least upon the medical factors, subjective perceptions and operational aspects gathered for each of the plurality of patients.

49 Claims, 17 Drawing Sheets

U.S. PATENT DOCUMENTS

| | | | |
|---|---|---|---|
| 6,306,087 B1 * | 10/2001 | Barnhill et al. | 600/300 |
| 6,317,731 B1 * | 11/2001 | Luciano | 706/21 |
| 6,370,234 B1 | 4/2002 | Kroll | |
| 6,786,406 B1 * | 9/2004 | Maningas | 235/385 |
| 6,819,785 B1 * | 11/2004 | Vining et al. | 382/128 |
| 7,222,066 B1 * | 5/2007 | Oon | 704/9 |
| 7,260,480 B1 * | 8/2007 | Brown et al. | 702/19 |
| 2002/0072911 A1 | 6/2002 | Kilgore et al. | |
| 2003/0079746 A1 * | 5/2003 | Hickle | 128/203.12 |
| 2003/0097278 A1 | 5/2003 | Mantilla et al. | |
| 2003/0163351 A1 | 8/2003 | Brown et al. | |
| 2003/0212580 A1 | 11/2003 | Shen | |
| 2004/0019501 A1 | 1/2004 | White | |
| 2004/0078223 A1 | 4/2004 | Sacco et al. | |
| 2004/0122296 A1 | 6/2004 | Hatlestad et al. | |
| 2004/0172291 A1 | 9/2004 | Knowlton | |
| 2005/0137929 A1 * | 6/2005 | Frazier et al. | 705/9 |
| 2006/0074711 A1 * | 4/2006 | Mahesh et al. | 705/2 |
| 2006/0167721 A1 * | 7/2006 | Bernard et al. | 705/2 |
| 2007/0038474 A1 | 2/2007 | Halsted | |
| 2007/0116336 A1 * | 5/2007 | Mahesh et al. | 382/128 |
| 2007/0156456 A1 * | 7/2007 | McGillin et al. | 705/2 |

OTHER PUBLICATIONS

Final Office Action in U.S. Appl. No. 11/501,468 issued on Oct. 14, 2010.

U.S. Appl. No. 11/501,468.

* cited by examiner

ARTS - Automated Radiology Triage System

| Outpatient Case List | Enter New Patient Information | All Current Cases | Logout |

Service: Outpatient Mason

Give Us Your Feedback

08/16/2004 - Unassigned & Assigned Mason Patient List:

| Patient Name | Study Type | Status | Estimated Time to Report | Assigned Technologist | Assigned Radiologist |
|---|---|---|---|---|---|
| Walker, Jim | Chest | Unassigned | 10:13 | Elmore, Miranda | Not Yet Assigned |
| Rogers, Steve | Hip | Assigned | 08:23 | Baldwin, Lindsey | Kraus, Steven |
| Murdock, Mathew | Foot | Assigned | 08:20 | Altenburger Stacy | Fodor, Daniel |
| Parker, Peter | Elbow | Unassigned | 10:19 | Alisp, Chris | Not Yet Assigned |

08/16/2004 - Reported & PPL-Completed Mason Patient List

| Patient Name | Study Type | Status | Time Case Entered | Actual Time Reported | Assigned Technologist | Requesting MD |
|---|---|---|---|---|---|---|
| Fiddich, Glen | Abd | Patient Case Passed to PPL | 07:56 | 09:00 | Aylor, Carrie | Mallory, Mia L., M.D. |

ARTS – Automated Radiology Triage System  Service: Outpatient Mason

Outpatient Case List | View Case Information | All Current Cases | Logout

Give Us Your Feedback — 106

Edit Case Information

Patient Information — 104
- Name:
- MR#:
- D.O.B.:
- Age:
- Study Type:
- History: Abdominal Pain

Requesting MD Information — 110
- Name:
- Phone:
- Pager:
- Other:

Assigned Technologist Information — 108
- Name: Elhore, Moranda
- Contact:
- Tech Comments: Fell over the handle bars of his bike.

Assigned Radiologist Information
- Name: NOT YET ASSIGNED
- Pager:

Patient Acuity Scores — 112

| Requested Acuity | Medical Acuity | Patient Waiting? |
|---|---|---|
| ⦿ STAT / ○ NON-STAT | ○ Airway / ⦿ Major Trauma / ○ Fracture / ○ Pneumonia / ○ Routine | ⦿ Yes / ○ No |

| Subjective Acuity | | Patient/Parent Anxiety |
| ○ Extreme / ⦿ Moderate / ○ Mild | | ⦿ High / ○ Low |

| | | Requesting MD Anxiety |
| | | ⦿ Anxious / ○ Calm |

ARTS - Automated Radiology Triage System

Servic: Radiology Room

Give Us Your Feedback

| Radiology Reading Room Assistant | Radiologist | Reported Cases | All Current Cases | Logout |

>>> *Patient Cases Passed back from PPL (see "Status")*

| Patient Name | Study Type | Status | Time Case Entered | Actual Time Reported | Assigned Technologist | Requesting MD |
|---|---|---|---|---|---|---|
| Murdock, Mathew | Foot | From PPL DocWantsConsult | 08:53 | 08:58 | Clark, Andrea | Banner, Bruce |

Assigned Patient Case List

| Unassign Case | Radiologist Name | Patient Name | Study Type | Requesting MD | Site | Estimated Time to Report | Routing |
|---|---|---|---|---|---|---|---|
| unassign | Grahm, Willson | Parker, Peter | Elbow | Strangelove | OPN | 09:47 | NON-PPL |

| | Patient/Case Information | | | | | | | | | Please Provide the Following | |
|---|---|---|---|---|---|---|---|---|---|---|---|
| Case # | Patient Age | Type | Subjective Acuity | Medical Acuity | Patient Waiting | Patient Anxiety | Refg MD Anxiety | Add'l View | | Urgency Score (100 = Extreme 1 = None) | Rank 5 most Urgent |
| 1 | 18 wk | Chest | Mild | Pneum | No | Low | High | No | Shortness of breath for two days | | |
| 2 | 4 mo | Chest | Extreme | Trauma | Yes | High | High | No | MVA 1 hour ago | | |
| 3 | 8 yr | Abd | Moderate | Routine | No | High | High | No | Abdominal pain | | |
| 4 | 18 mo | Chest | Mild | Airway | No | Low | Low | Yes | Cough | | |
| 5 | 6 yr | Knee | Extreme | Fracture | Yes | Low | High | No | Fall on playground 4 hours ago | | |
| 6 | 17 yr | Chest | Extreme | Trauma | Yes | High | High | Yes | MVA | | |
| 7 | 5 yr | Abd | Extreme | Routine | Yes | Low | Low | No | Acute onset Abdominal pain | | |
| 8 | 9 yr | Rad/ulna | Extreme | Fracture | No | Low | High | No | Arm bent after soccer collision | | |
| 9 | 5 wk | Femur | Extreme | Fracture | No | High | High | No | Fell off changing table | | |
| 10 | 12 yr | Knee | Moderate | Routine | Yes | High | High | No | Knee pain | | |
| 11 | 14 yr | Tib/Fib | Mild | Routine | No | Low | High | No | Lump adjacent to tibia | | |
| 12 | 11 yr | Foot | Moderate | Routine | Yes | Low | Low | No | stepped on nail 3 days ago, still has pain | | |
| 13 | 16 yr | L Spine | Extreme | Trauma | Yes | High | Low | Yes | fell off horse- back pain | | |
| 14 | 18 mo | Chest | Mild | Pneum | No | Low | High | No | cough | | |
| 15 | 17 yr | Skull | Mild | Trauma | Yes | Low | High | Yes | Bike accident | | |
| 16 | 6 yr | Chest | Mild | Trauma | Yes | Low | High | No | Near drowning | | |
| 17 | 15 mo | Femur | Mild | Trauma | Yes | High | High | No | Fall from tree | | |
| 18 | 18 mo | Airway | Extreme | Airway | Yes | Low | Low | Yes | Sever stridor | | |
| 19 | 12 yr | Chest | Mild | Airway | No | Low | Low | Yes | Cough | | |
| 20 | 12 yr | Ankle | Moderate | Trauma | Yes | Low | Low | No | Soccer collision | | |

FIG. 16

Patient/Case Information

| Case # | Patient Age | Type | Subjective Acuity | Medical Acuity | Patient Waiting | Patient Anxiety | Refg MD Anxiety | Add'l View | | This is how your colleague ranked these cases: | Plea note here any changes you would make to the rankings: |
|---|---|---|---|---|---|---|---|---|---|---|---|
| 1 | 18 wk | Chest | Mild | Pneum | No | Low | High | No | Shortness of breath for two days | 1 | |
| 2 | 4 mo | Chest | Extreme | Trauma | Yes | High | High | No | MVA 1 hour ago | 2 | |
| 3 | 8 yr | Abd | Moderate | Routine | No | High | High | No | Abdominal pain | 3 | |
| 4 | 18 mo | Chest | Mild | Airway | No | Low | Low | Yes | Cough | 4 | |
| 5 | 6 yr | Knee | Extreme | Fracture | Yes | Low | High | No | Fall on playground 4 hours ago | 5 | |
| 6 | 17 yr | Chest | Extreme | Trauma | Yes | High | High | Yes | MVA | 6 | |
| 7 | 5 yr | Abd | Extreme | Routine | Yes | Low | Low | No | Acute onset Abdominal pain | 7 | |
| 8 | 9 yr | Rad/ulna | Extreme | Fracture | No | Low | High | No | Arm bent after soccer collision | 8 | |
| 9 | 5 wk | Femur | Extreme | Fracture | No | High | High | No | Fell off changing table | 9 | |
| 10 | 12 yr | Knee | Moderate | Routine | Yes | High | High | No | Knee pain | 10 | |

1. Overall, how well do you feel the list of cases is ordered in a way that has the most medically urgent cases (those needing to be read sooner) higher on the list with less urgent cases nearer the bottom (circle one)?

Completely acceptable      Mostly acceptable      Mostly unacceptable      Completely unacceptable 2. What changes would you make to the ranked list (in terms of how the cases are ordered)? Make any revisions in the right-most column in the table and describe below (continue on the back if necessary) why you made these changes.

FIG. 17

AUTOMATED SYSTEM AND METHOD FOR PRIORITIZATION OF WAITING PATIENTS

CROSS-REFERENCE TO RELATED APPLICATIONS

The present application is a continuations of and claims priority to and benefit of International (PCT) Application, Ser. No. PCT/US06/10660, filed Mar. 23, 2006, and U.S. Provisional Application Ser. No. 60/664,517, filed Mar. 23, 2005, which are herein incorporated by reference in their entirety.

BACKGROUND

The present invention provides a system and method for automated triage; and more specifically, an automated system and method that utilizes both subjective and objective criteria in the prioritization algorithm.

Automated decision-making systems have the potential simultaneously to improve the quality of patient care and reduce medical costs. Medical services, including radiology, routinely rely on physicians and other highly trained personnel to make routine and repetitive decisions. One such situation is a prioritization, or triage, of waiting patients or cases. When done manually, this triage process is inherently time consuming. This reduces the amount of medical staff available to provide patient care.

Conventionally, radiologists in a central "reading room" interpret exams received in a first-in first-served basis. Furthermore, for various reasons, the radiologists are often interrupted with requests for expedited examination of certain cases and/or requests for status on cases that are being examined or have yet to be examined. This, of course, drastically reduces the efficiency of the examination process and increases the stress level of the radiologists and all others involved in the process.

Additionally, a manual triage process can be inherently inconsistent, varying from decision-maker to decision-maker. This can put patients with urgent needs at risk and waiting longer than is medically appropriate or necessary. However, there is no well-established model for developing an effective automated decision-making system for assisting radiological triage based on both medical and operational factors. Moreover, there is no generally accepted methodology for measuring the operational and perceptual effects produced by such system. Without effective and efficient technology-enabled decision-making systems, radiological triage (and medical triage in general) will remain burdensome, unreliable, and costly.

SUMMARY

The present invention provides an automated triage system that will improve the quality of patient care and the well-being and effectiveness of medical personnel. The central hypothesis of the invention is that the dissemination of the real-time status information produced by a computerized, algorithm-based prioritization system (that is able to make appropriate triage decisions faster and more consistently than a triage process relying on physicians and/or other medical personnel) will have three effects: (a) decreased average examination time, (b) increased staff satisfaction, and (c) increased patient satisfaction. This hypothesis is based upon an initial observation that the lack of a consistent triage process, and the resulting deficiency of case status information, leads to increased interruptions of medical personnel, which increases examination times and degrades the working environment. The present invention enables medical services to deliver better and more efficient patient care while simultaneously improving working conditions for medical personnel.

It is a first aspect of the invention to provide a computerized method for automated prioritization of waiting patients. The method includes the steps of: (1) for plurality of patients, gathering with the assistance of a computer at least one medical factor associated with each patient's medical condition, where the medical condition is (a) a type of injury, (b) a symptom, (c) a condition of a patient, and/or (d) a demographic statistic of the patient; (2) for the same plurality of patients, gathering with the assistance of a computer at least one subjective perception associated with each patient's medical condition, which may be (a) the anxiety of the patient, (b) the anxiety/concern of the referring physician, or and/or (c) the anxiety of the reviewing attendee; and (3) ordering, by a computerized algorithm, the plurality of patients for medical treatment and/or medical assessment, based upon the medical factors and subjective perceptions gathered for each of the plurality of patients.

In a further detailed embodiment, the method further includes the steps of: (4) for a new patient, gathering with the assistance of a computer at least one medical factor associated with the new patient's medical condition, where the medical factor is (a) a type of injury, (b) a symptom, (c) a condition of the new patient and/or (d) a demographic statistic of the new patient; (5) for the new patient, gathering with the assistance of a computer at least one subjective perception associated with the new patient's medical condition, where the subjective perception is (a) the anxiety of the new patient, (b) the anxiety/concern of the referring physician and/or (c) the anxiety/concern of reviewing attendee; and (6) reordering, by the computerized algorithm, the plurality of patients and the new patient for medical treatment and/or medical assessment, based upon the medical factors and the subjective perceptions gathered for the plurality of patients and the new patient.

In an alternate detailed embodiment of the first aspect of the present invention, the method further includes a step of displaying the ordered plurality of patients to an individual associated with providing the medical treatment and/or medical assessment. In a further detailed embodiment, the method includes a step of indicating with the assistance of a computer that a patient in the ordered display has received the medical treatment and/or medical assessment. In a further detailed embodiment, the method further includes a step of reordering, by the computerized algorithm, the plurality of patients, less the indicated patient, for medical treatment and/or medical assessment, based upon the medical factors and subjective perceptions gathered for each of the plurality of patients, less the indicated patient.

In another alternate detailed embodiment of the first aspect of the present invention, the method further includes the step of displaying the ordered plurality of patients on the display viewable by one or more of the plurality of patients or by a waiting room receptionist (who can provide realistic estimates to waiting patients wondering how much more time will be necessary to complete the exam). In a further detailed embodiment, this display is viewable by the persons situated within a waiting room, where the identity of each patient on the display will be preferably coded to protect the patient's confidentiality. Similarly, each patient may be given a hand-held device (such as a pager device) that will be automatically updated by the system of the present invention with an approximate time remaining for the exam and/or will provide an alert to the waiting patient when the exam results are ready.

Such updates may also be wirelessly transmitted to the waiting patient's cell-phone or other hand-held computer device.

And yet a further alternate detailed embodiment of the first aspect of the present invention, the method further includes the step of, for the plurality of patients, gathering with the assistance of a computer at least one operational aspect, which may include (a) waiting time of the patient, (b) medical treatment facilities availability, (c) medical treatment staff availability, (d) medical assessment facilities availability, and/or (e) medical assessment staff availability; where the ordering step includes the step of ordering, by the computer algorithm, the plurality of patients for medical treatment and/or medical assessment, based at least upon the medical factors, subjective perceptions and operational aspects gathered for each of the plurality of patients.

In yet a further detailed embodiment of the first aspect of the present invention, the computerized algorithm applies weights to certain of the gathered medical factors and subjective perceptions in the ordering steps and the weights are based upon mental heuristics collected from a plurality of experienced professionals who perform the medical treatment/medical assessment on a regular basis. In a further detailed embodiment, the algorithm generates an acuity score and the patients are ordered based upon, at least in part, the generated acuity score, and the algorithm generates a more urgent acuity score if the patient is waiting. In a further detailed embodiment, the algorithm generates a more urgent acuity score if the patient's anxiety is relatively high. In yet a further detailed embodiment, the algorithm generates a more urgent acuity score if the anxiety of the referring physician and/or the anxiety of the reviewing attendee is high. In yet a further detailed embodiment, the algorithm generates a more urgent acuity score depending upon a perceived severity of the type of injury. The algorithm may also generate a more urgent acuity score depending upon the amount of time the patient has been waiting, and the urgency may rise exponentially in relation to the amount of time the patient has been waiting.

In yet another alternate detailed embodiment of the first aspect of the present invention, the method further includes the step of estimating a waiting time for each of the plurality of patients. In a more detailed embodiment, the step of estimating a waiting time for each of the plurality of patients is based upon a consideration of: (i) an average medical treatment or medical assessment time for previous patients and (ii) a number of patients ahead of a given patient in the ordered plurality of patients. In an even further detailed embodiment, the average medical treatment or medical assessment time is a rolling average. In an even further detailed embodiment, the method further includes the step of displaying the ordered plurality of patients on a viewable display and including the estimated waiting time for each patient in the display. Alternatively, the method further includes the step of communicating an estimated waiting time to a corresponding waiting patient. In certain detailed embodiments, these estimating, displaying and/or communicating steps are repeated periodically so as to have a constantly updated and accurate waiting time estimate.

It is a second aspect of the present invention to provide a method for prioritization of waiting patients that includes the steps of: (1) for a plurality of patients, gathering with the assistance of a computer medical factor(s) associated with each patient's medical condition such as (a) a type of injury, (b) a symptom, (c) a condition of the patient, (d) a reason for seeking a medical treatment, and/or (e) a reason for seeking a medical assessment; (2) for the plurality of patients, gathering with the assistance of a computer demographic item(s) associated with each patient; (2) for the plurality of the patients, gathering with the assistance of a computer operational aspect(s) such as (a) whether the patient is waiting or not, (b) waiting time of the patient, (c) medical treatment facilities availability, (d) medical treatment staff availability, (e) medical assessment facilities availability, and/or (f) medical assessment staff availability; and (4) ordering, by a computerized algorithm, the plurality of patients for medical treatment and/or medical assessment, based at least upon a combination of the operational aspect(s) and at least one of the medical factor(s) and/or the demographic item(s) gathered for each of the plurality of patients.

In a more detailed embodiment of the second aspect of the present invention, the method further includes the step of, (5) for the plurality of the patients, gathering with the assistance of a computer subjective perception(s) associated each patient's medical condition such as, (a) anxiety of the patient, (b) anxiety of the referring physician, and/or (c) anxiety of the reviewing attendee; where the ordering step includes the step of ordering, by the computerized algorithm, the plurality of patients for medical treatment and/or medical assessment, based at least upon a combination of the operational aspect(s) with the medical factor(s), and/or the demographic item(s) and/or the subjective perception(s) gathered for each of the plurality of patients. In a further detailed embodiment, the algorithm applies weights to the operational aspect(s), the medical factor(s), the demographic item(s) and the subjective perception(s) in the ordering steps; and the weights are based upon mental heuristics of a plurality of experienced professionals who perform the medical treatment and/or medical assessment.

It is a third aspect of the present invention to provide a method for automated prioritization of waiting patients that includes the steps of: (1) ordering, by a computerized algorithm, a plurality of patients for medical treatment and/or medical assessment, based at least upon a combination of two or more of, (i) at least one operational aspect, (ii) at least one medical factor, (iii) at least one demographic item, and (iv) at least one subjective perception gathered for each of the plurality of patients; (2) the algorithm applies weights to the two or more of, (i) the at least one operational aspect, (ii) the at least one medical factor, (iii) the at least one demographic item, and (iv) the at least one subjective perception gathered for each of the plurality of patients; and (3) collecting mental heuristics of a plurality of experienced professionals who perform the medical treatment and/or medical assessment; and (4) calculating the weights based upon, at least in part, the collected mental heuristics; where the operational aspect(s) may be (a) whether the patient is waiting or not, (b) waiting time of the patient, (c) medical treatment facilities availability, (d) medical treatment staff availability, (e) medical assessment facilities availability, and/or (f) medical assessment staff availability; where the medical factor(s) may be (a) a type of injury, (b) a symptom, (c) a condition of the patient, (d) a reason for seeking a medical treatment, and/or (e) a reason for seeking a medical assessment; and where the subjective perception(s) may be (a) anxiety of the patient, (b) anxiety of the referring physician, and/or (c) anxiety of the reviewing attendee.

In a more detailed embodiment of the third aspect of the present invention, the step of collecting mental heuristics of a plurality of experienced professionals include the steps of: providing to a first group of experienced medical professionals a form that includes a first plurality of test-cases; and rating by each of the first group of experienced medical professionals each of the test-cases in the form, where the rating is based upon a level of urgency perceived for each test-case.

In a further detailed embodiment, each test case in the first plurality of test-cases includes (i) at least one hypothetical indication of operational aspect, (ii) at least one hypothetical indication of a medical factor, (iii) at least one hypothetical demographic item, and (iv) at least one hypothetical indication of a subjective perception. Alternatively, each test case in the first plurality of test-cases includes (i) at least one hypothetical indication of operational aspect, (ii) at least one hypothetical indication of a medical factor, and (iii) at least one hypothetical indication of a subjective perception. Alternatively, the method further includes the steps of generating a test-set of weights from the ratings provided by the first group of experienced professionals; ordering a second plurality of hypothetical test-cases using the test-set of weights; providing the ordered second plurality of hypothetical test-cases to a second group of experienced medical professionals for review by the second group of experienced medical professionals; and from the results of the review by the second group of experienced medical professionals, generating the weights to be applied to, (i) the operational aspect(s), (ii) the medical factor(s), (iii) the demographic item(s), and/or (iv) the subjective perception(s) gathered for each of the plurality of patients.

It is a fourth aspect of the present invention to provide a method for processing radiology cases that includes the steps of: providing a software tool on a computer server (for the purposes of the present invention a "computer server" can be one or more computers, computer systems or computer servers, such as Web servers for example, that alone or collectively provide the software tool and associated records and files) accessible by a plurality of workstations (for the purposes of the present invention a "workstation" is any computer or device, such as a Web enabled device for example, capable of accessing at least portions of the software tool over a data network such as a computer network, the internet, or a cellular network for example) coupled to the computer server over a computer network, wherein the software tool has access to a plurality of radiology case files corresponding to a plurality of pending radiology cases, and wherein the plurality of radiology case files includes information sufficient for one or more radiologists to conduct radiological examinations on the plurality of pending radiology cases; assigning, with the assistance of the software tool, one or more of the plurality of pending radiology cases to a first radiologist and one or more of the remaining plurality of pending radiology cases to a second radiologist; accessing the software tool over the computer network by the first radiologist utilizing a first one of a plurality of workstations to view one or more radiology case files pertaining to a pending radiology case assigned to the first radiologist, and recording an examination of the pending radiology case assigned to the first radiologist in the software tool by the first radiologist utilizing the first one of the plurality of workstations; removing, by the software tool, the pending radiology case assigned to the first radiologist from the plurality of pending radiology cases; accessing the software tool over the computer network by the second radiologist utilizing a second one of a plurality of workstations to view one or more radiology case files pertaining to a pending radiology case assigned to the second radiologist, and recording an examination of the pending radiology case assigned to the second radiologist in the software tool by the second radiologist utilizing the second one of the plurality of workstations; and removing, by the software tool, the pending radiology case assigned to the second radiologist from the plurality of pending radiology cases.

In a more detailed embodiment, the method of the fourth aspect further includes the steps of communicating at least one of the recorded examinations recorded by at least one of the first and second radiologists to a referring physician; and storing a record of the communicating step, by or with the assistance of the software tool. In a more detailed embodiment, the communicating step includes the step of accessing, with the assistance of the software tool and utilizing a third one of the plurality of workstations, the recorded examinations recorded by at least one of the first and second radiologists by a communication assistant responsible for communicating data from the recorded examinations to the referring physician; and the step of storing a record of the communication step includes a step of recording by the communication assistant, with the assistance of the software tool and utilizing the third one of the plurality of workstations, a record of communications with the referring physician.

In an alternate detailed embodiment of the fourth aspect the assigning step includes a step of accessing, with the assistance of the software tool and utilizing a third one of the plurality of workstations, a graphical user interface that provides list of the plurality of pending radiology cases by an third individual, and utilizing the graphical user interface to assign from the list one or more of the plurality of pending radiology cases to a first radiologist and one or more of the remaining plurality of pending radiology cases to a second radiologist. In a more detailed embodiment, the list is ordered on the graphical user interface according to an acuity algorithm output.

In another detailed embodiment of the fourth aspect the assigning step includes a step of accessing, with the assistance of the software tool and utilizing one of the plurality of workstations, a graphical user interface that provides list of the plurality of pending radiology cases by the first radiologist, and utilizing the graphical user interface to assign from the list one or more of the plurality of pending radiology cases to the first radiologist. In a more detailed embodiment, the list is ordered on the graphical user interface according to an acuity algorithm output.

In another detailed embodiment of the fourth aspect the assigning step includes a step of providing a graphical user interface by the software tool that provides a prioritized list of the plurality of pending radiology cases. In a more detailed embodiment, the prioritized list is generated by the software tool utilizing an acuity algorithm that calculates priority based at least upon a combination of at least one medical factor and at least one subjective perception gathered for each of the plurality of pending radiology cases; the at least one medical factor is (a) a type of injury, (b) a symptom, (c) a condition of the patient, and/or (d) a demographic statistic of the patient; and the at least one subjective perception is (a) anxiety of the patient, (b) anxiety of the referring physician, (c) anxiety of the reviewing attendee, and/or (d) whether the referring physician ordered the case STAT. In a further detailed embodiment, the acuity algorithm further calculates priority based at least one operational aspect, where the at least one operational aspect is (a) whether the patient is waiting or not, (b) the waiting time of the patient, (c) the medical treatment facilities availability, (d) the medical treatment staff availability, (e) the medical assessment facilities availability, and/or (f) the medical assessment staff availability.

In another detailed embodiment, the prioritized list is generated by the software tool utilizing an acuity algorithm that calculates priority based at least upon one aspect gathered for each of the plurality of pending radiology cases; the at least one aspect is (a) whether the patient is waiting or not, (b) the waiting time of the patient, and/or (c) whether the referring physician ordered the case STAT. In a further detailed embodiment, the acuity algorithm calculates priority based at least upon a combination of (a) whether the patient is waiting or not, (b) waiting time of the patient, and (c) whether the referring physician ordered the case STAT.

BRIEF DESCRIPTION OF THE DRAWINGS

FIG. 3 is an exemplary screen shot for "view cases" object operating on a technologist workstation;

FIG. 4 is an exemplary screen shot of a "view case details" object operating on a technologist's workstation;

FIG. 9 is an exemplary screen shot of a "view cases" object operating on a radiologist's workstation;

FIG. 11 is an exemplary screen shot of a "contact record" object operating on a radiologist's workstation;

Figure 12:
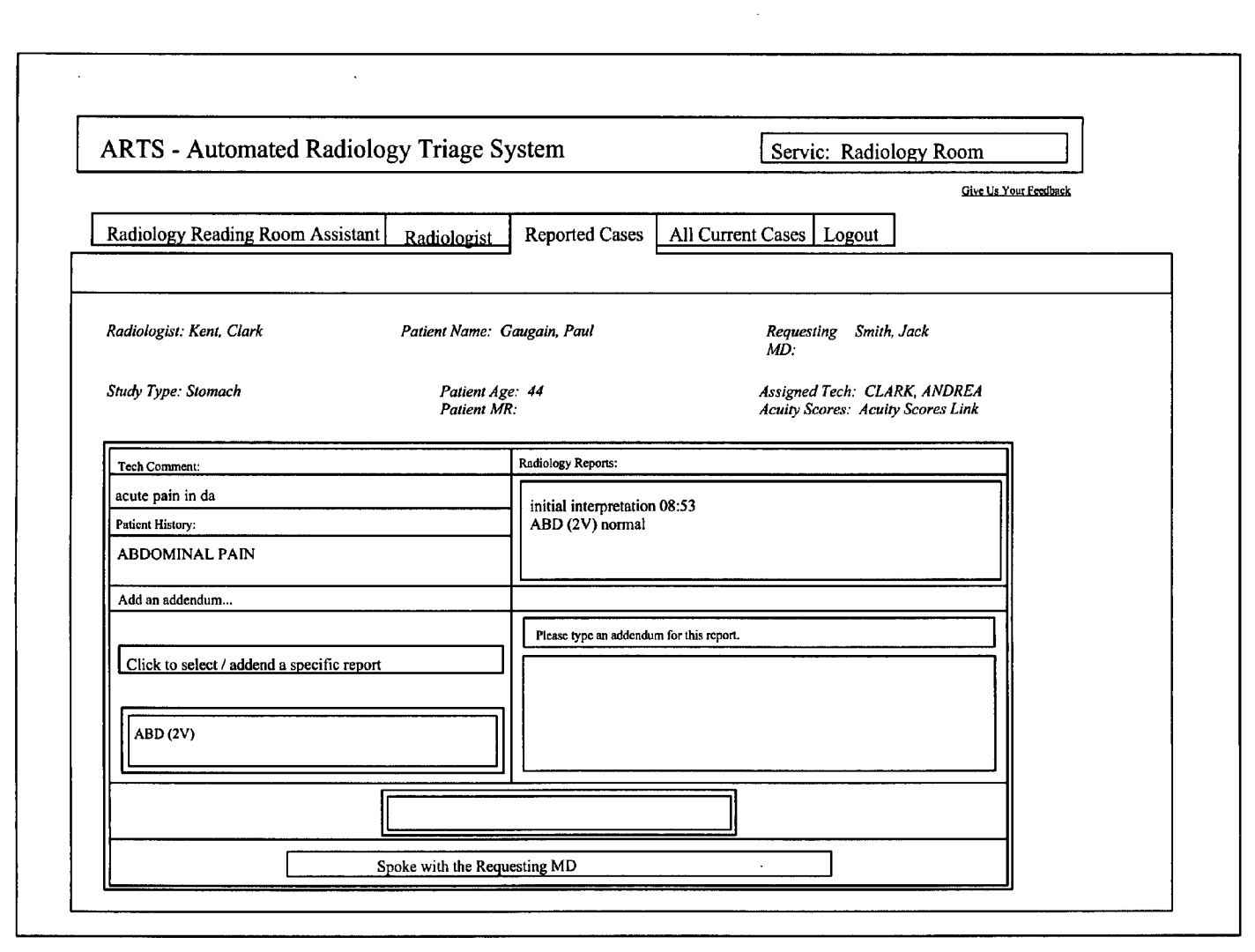

FIG. 12 is an exemplary screen shot of a "view reported cases" object operating on a radiologist's workstation;

FIG. 15 is an exemplary screen shot of an "add addendum" object operating on the radiologist's workstation;

FIG. 16 is an exemplary screen shot of acuity score worksheet for use with an exemplary embodiment of the present invention; and FIG. 17 is an exemplary embodiment of another acuity score worksheet for use with an exemplary embodiment of the present invention.

DETAILED DESCRIPTION

Exemplary embodiments described herein pertain to an automated radiology triage system ("ARTS"), which pertains to a computerized system and method for prioritizing radiological examinations of cases using an algorithm that is based upon mental heuristics of actual radiologists and/or is based upon a combination of objective medical factors and subjective perceptions associated with each case. While the exemplary embodiments described herein pertain to such radiological triage, it will be apparent to those of ordinary skill in the art that the invention may be used to prioritize/triage other types of medical examinations and/or treatments; and may also be used to prioritize events and other activities occurring outside of the medical field. Examples of such alternate prioritization purposes include health care applications, such as urgent-care centers, emergency rooms/departments and pharmacies; consumer service applications, such as automotive repair facilities; and the like.

Figure 1:
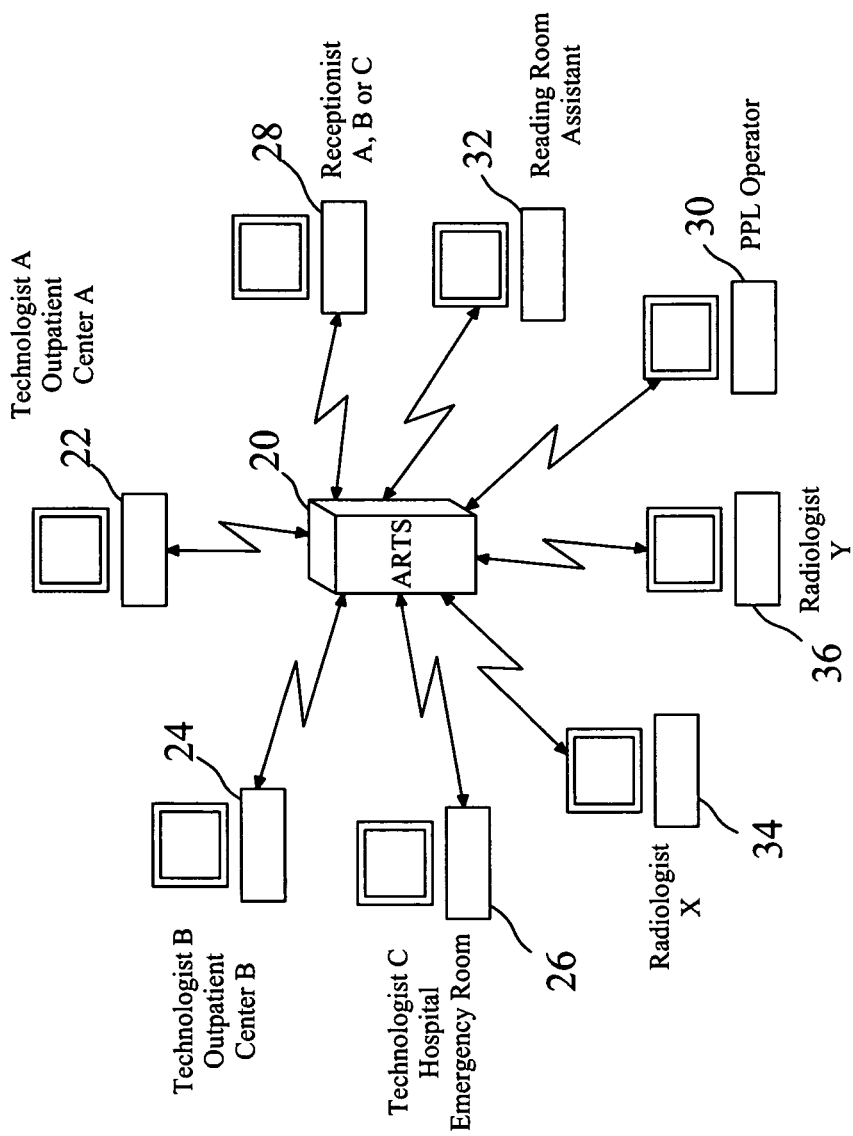
FIG. 1 is a schematic block diagram representation of an exemplary network system for implementing the present invention.

As shown in FIG. 1, the automated radiology treatment triage system ("ARTS") exists as a software tool residing on a central server 20, which may be accessed by one or more workstations operatively coupled to the central computer through a direct connection or a network connection (wired or wireless). For example, in the exemplary embodiment, the ARTS tool is a web-based application accessible by the plurality of workstations over the internet. In the present exemplary embodiment, the plurality of workstations accessing the ARTS tool includes "Technologist A" 22 at an outpatient center A, "Technologist B" 24 at another remote outpatient center B, and "Technologist C" 26 at a hospital emergency room. Each of these remote outpatient centers and/or hospital emergency rooms may also include a receptionist workstation 28. A physician priority link ("PPL") operator 30 has access to the ARTS system as well as a reading room assistant 32. Finally, a number of radiologists 34, 36 have access to the ARTS system as will be described in further detail below.

Figure 2:
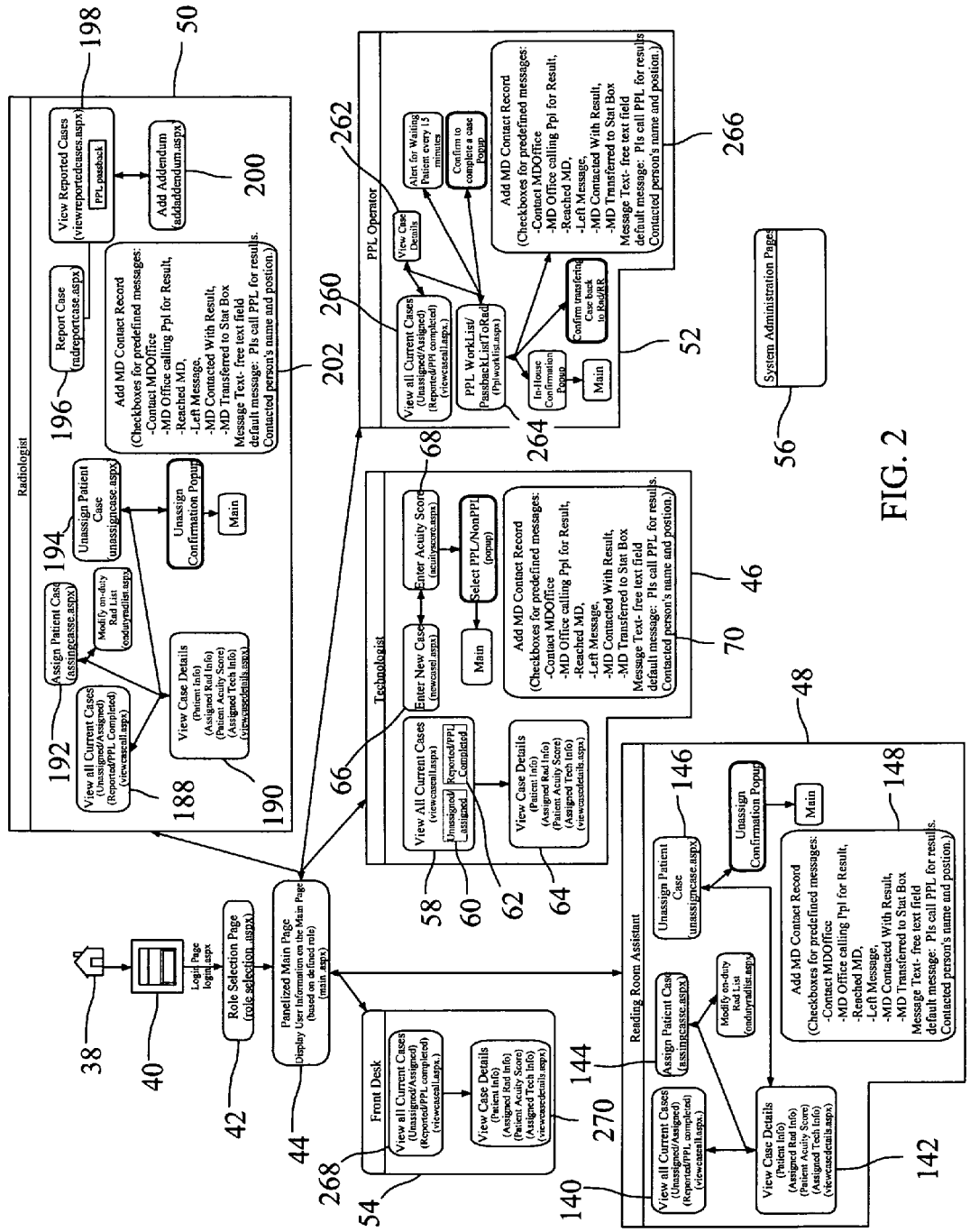
FIG. 2 is a schematic block diagram representation of the software object structure according to an exemplary embodiment of the present invention.

As shown in FIG. 2, operation of the ARTS tool on the server 20 initially provides to anyone accessing its home page 38, a login page 40, which will typically request a user name and password from the individual seeking access. Once logged in, a role selection object 42 will be implemented that will either automatically determine the role of the individual logging in or allow the individual to select a role from a list of rolls. Once selected, the user will be provided with a main page 44 which is personalized for the individual user and the user's roll. In the exemplary embodiment, the available rolls include a technologist's role 46, a reading room assistant's role 48, a radiologists' role 50, a PPL role 52, a front desk/receptionist role 54 and system administrator role 56.

Generally, the process overview includes a technologist (in an outpatient center, for example) accessing a technologist's object 46 on the ARTS system to initialize a patient in the ARTS system and to complete an initial exam of the patient, which includes entering certain acuity level factors in the ARTS system as will be described in detail below. The ARTS system will then prioritize each of the plurality of patients present in the ARTS system based upon an acuity prioritization algorithm that will also be discussed in further detail below. A reading room assistant at workstation 32 accessing the reading room assistant object 48 will monitor the prioritized list of patients and assign cases in the prioritized list to available radiologists based upon the priority of the case and the availability of the particular radiologist. The ARTS system also allows the radiologists at workstations 34 and 36 through the radiologist object 50 to view the prioritized list of patients and to assign cases in the prioritized list to themselves. Each radiologist at workstations 34 and 36, will then access the ARTS system through the radiologist object 50 to access the assigned list of cases he or she is to examine, access all the records and files necessary to perform the particular examination, and then record his or her examination into the ARTS system, subsequent to which the patient will be removed from the prioritization list and added to a "to contact" list. Finally, the ARTS system provides the capability for each individual working with the system to provide contact reports such as MD contact records to memorialize all communications between the various individuals for record keeping purposes.

The technologist's desktop 46 includes a "view cases" object 58 which may be used to view assigned and/or unassigned cases 60 and review reported/PPL completed cases 62 and which provides the technologist with the ability to bring up a "view case details" object 64 for reviewing patient information, referring MD information, assigned radiology information, patient acuity scores, assigned technologist information, and other details. The technologist desktop also includes an "enter new case" object 66, which leads to an "enter acuity score" object 68. Finally, the desktop includes an "add MD contact record" object 70.

As shown in FIG. 3, a screen shot of the "view all current cases" object 58 on the technologist's desktop 46 provides a field 72 indicating the location of the technologist—in this case, the Mason Outpatient Center. The "view all current cases" object 58 also includes a table 74 listing all the unassigned, assigned cases and completed cases for the particular outpatient center. This table 74 includes a patient name column 76, a study type column 78, an assigned/unassigned column 80, an estimated time to report column 82, an assigned technologist column 84, and an assigned radiologist column 86.

As will be discussed in further detail below, the status column 80 refers to whether the reading room assistant has assigned the case to a radiologist or not or whether the case has been self-assigned by a radiologist. In this table 74 as with the other tables described herein, the list of patients are organized top-bottom based upon the relative acuity of each patient as assigned by the ARTS prioritization algorithm. This prioritization algorithm will be described in further detail below. In the exemplary embodiment, the most acute exams are at the top of the list and are presented with a red background. Less acute exams follow in various shades of red and pink, where the least acute exam appears at the bottom in light pink. In the exemplary embodiment, if the technologist wishes to open an exam and view information about the exam, the technologist merely needs to double click (activate) the patient's name in the table. Once activated, the "view case details" object 64 will be implemented. An exemplary screen shot of this "view case details" object 64 is shown in FIG. 4.

The "view all current cases" object 58 also includes a table 88 showing reported and PPL completed cases for the particular outpatient center. For each entry in this table 88, it means that a radiologist has entered a preliminary report into the ARTS system. This report has also been sent to Picture Archiving and Communication System ("PACS") and appears in the report window under "initial interpretation." This table includes a patient name column 90, a study type column 92, a status column 94, a time case entered column 96, an actual time recorded column 98, an assigned technologist column 100 and the requesting MD column 102.

A suitable RIS/PACS system for use with the present invention includes the Centricity™ RIS/PACS system commercially available through GE Healthcare. It is within the scope of the present invention that the radiologist will examine a particular case and then dictate a report (using voice-recognition tools), which populates written text in RIS/PACS database. The ARTS system, communicating with RIS/PACS, can then populate its own report log database using the report entered into the RIS/PACS database. For every new dictation or re-dictation into RIS/PACS, the process repeats and is logged by ARTS.

As shown in FIG. 4, the "view case details" screen provides a patient information table 104, a requesting MD information table 106, an assigned technologist information table 108, an assigned radiologist information table 110, and a patient acuity score table 112. If a patient's name is activated in the reported/PPL completed patient list table 88, the case information will include an assigned radiologist information table (not shown). This will include radiology report information, which will include the radiologist's report and the time it was entered. Any changes or addendums to the report will also be documented. For the technologist to enter new patient information, the technologist will activate the "enter new patient information" icon or tab 114 (see FIG. 3), which will activate the "enter new case" object 66.

Figure 5:
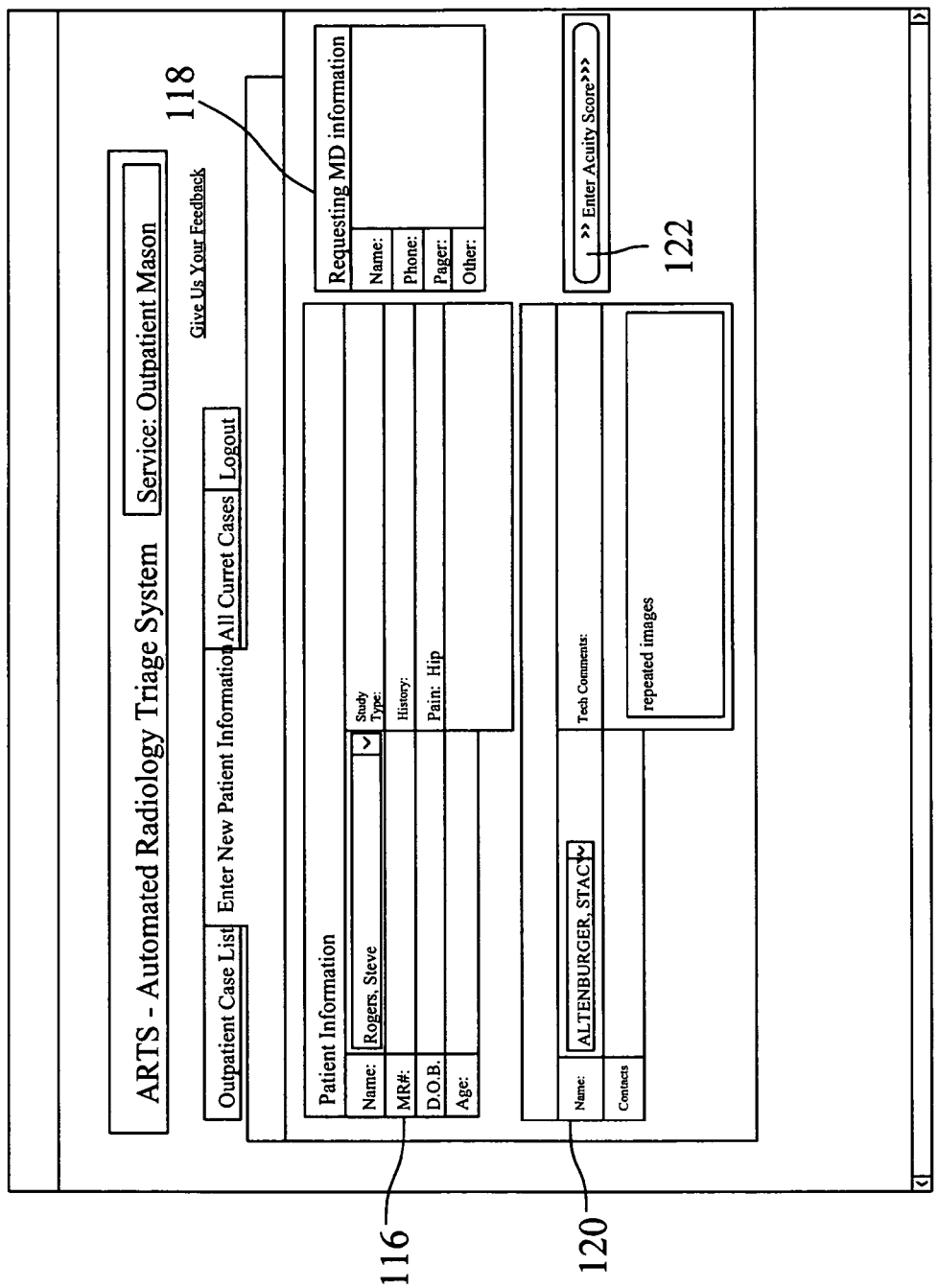
FIG. 5 is an exemplary screen shot of an "enter new case" object operating on the technologist's workstation.
Figure 6:
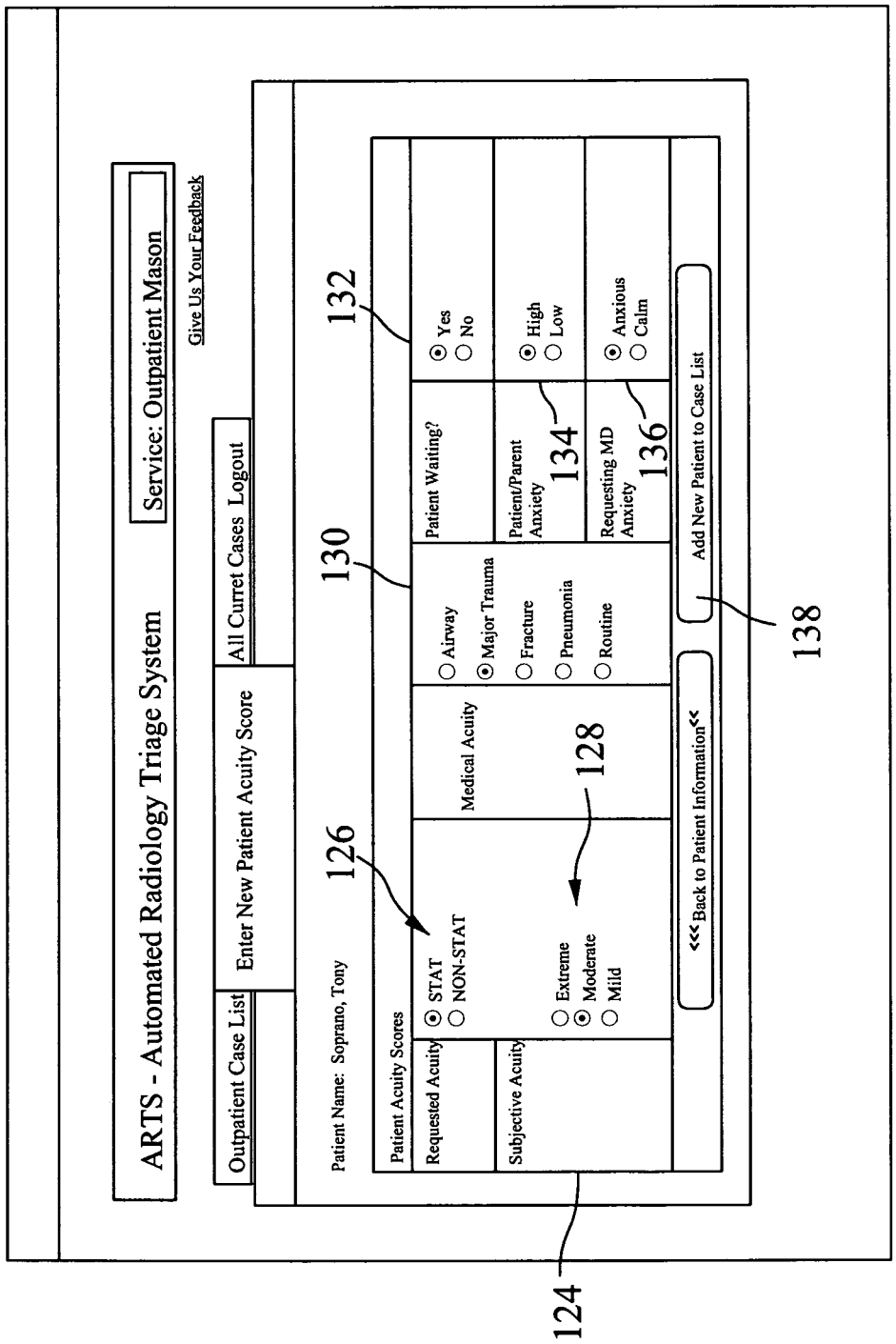
FIG. 6 is an exemplary screen shot of a "enter acuity score" object operating on the technologist's workstation.

As shown in FIG. 5, the "enter new case" object 66 will bring up a screen including a number of tables with information either preloaded (from a patient information database, for example) or requested from the technologist. The tables include a patient information table 116, a requesting MD information table 118, and an assigned technologist information table 120. An enter acuity score button 122 is also provided. When activated, the "enter acuity" object 68 will then be activated as shown in FIG. 6.

The "enter acuity" object will provide the technologist with the table into which the technologist will provide objective medical information, subjective acuity information, and certain operational information. Based upon these inputs, the prioritization algorithm will compute an acuity score for the patient so as to prioritize the patient with respect to the other patients in the ARTS system. As shown in FIG. 6, the acuity score table provides a field 126 requesting the technologist indicate whether the requested examination is to be STAT or non-STAT. The table also provides a field 128 requesting the technician to provide subjective acuity of the patient; and, specifically, to indicate whether the patient is under extreme acuity (difficulty breathing, for example), moderate acuity (significant pain, for example) or mild acuity (comfortable). A field 130 is provided requesting the technician to indicate an objective medical acuity characteristic, which requests the technician to select between "airway," "major trauma," "fracture," "pneumonia," or "routine." A field 132 requests the technician to indicate whether the patient is waiting or not. A field 134 requests the technician to indicate whether the patient and/or the parent is experiencing high or low anxiety; and another field 136 requests the technologists to indicate whether the requesting MD exhibits high or low anxiety/concern regarding the particular case. Once all of these fields have been filled by the technologist, the technologist will then activate the "add new patient to cases list" icon 138, after which the acuity data will be loaded into the ARTS system and the patient will be prioritized with the other patients provided therein.

The reading room assistant desktop 48 includes a "view all current cases" object 140 (similar to object 58 in the technologist desktop 46) a "view case details" object 142 (similar to object 64 in the technologist desktop 46) an "assign patient case" object 144 an "unassign patient case" object 146 and an "add MD contact record" object 148 (similar to object 70 in the technologist desktop 46).

Figure 7:
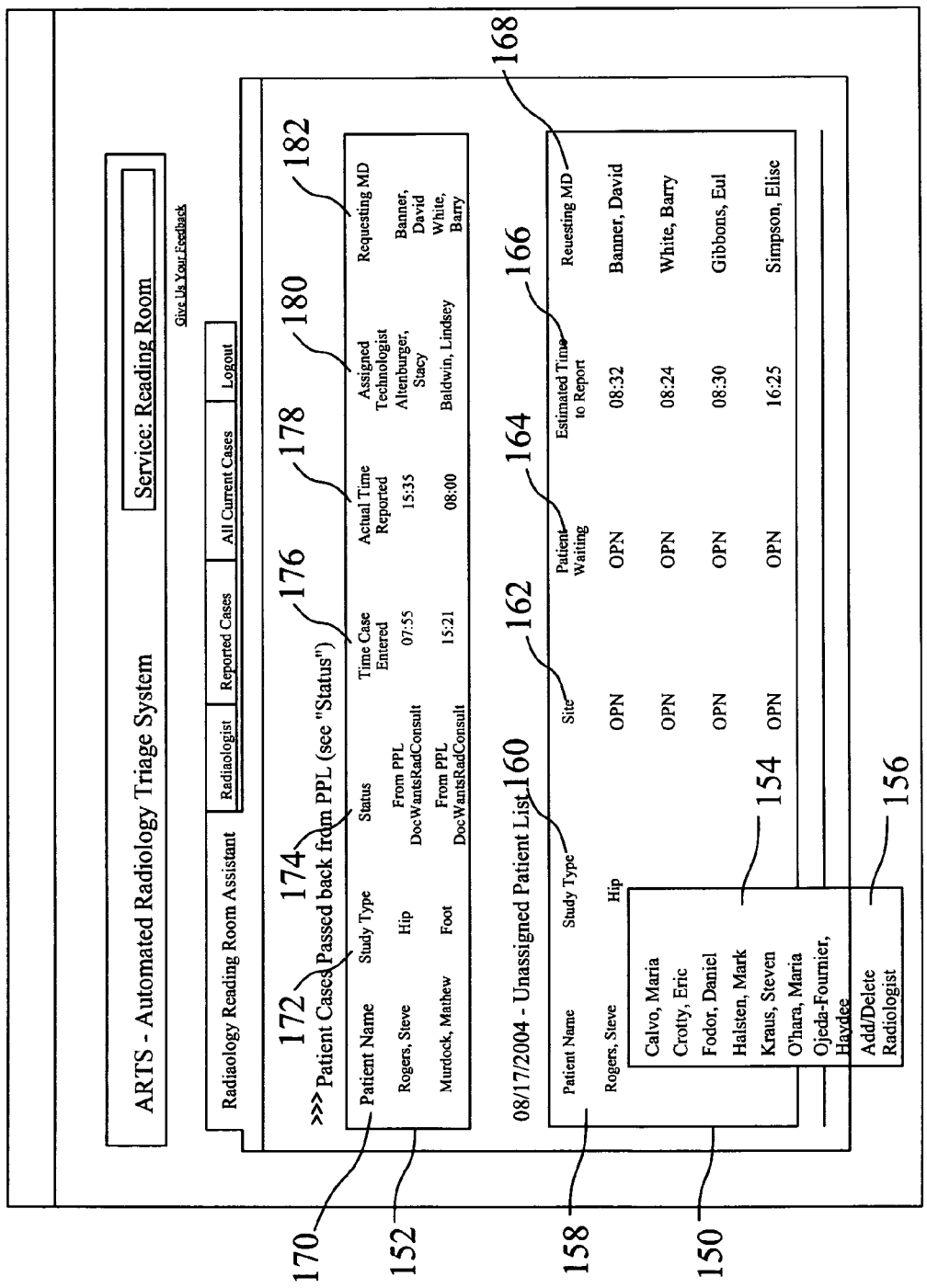
FIG. 7 is an exemplary screen shot of a "assign cases" object operating on a reading room assistant's workstation.

As shown FIG. 7, the "view all current cases" object 140 provides two work lists on the screen, an unassigned patient work list 150 and the work list 152 that lists patient exams that have been passed back Physician Priority Link ("PPL") for one of a variety of reasons, one example of which may be that the PPL operator is transferring the referring physician to the radiologist. This list 152 serves as a reminder that the call is coming and provides a way of completing the work flow in ARTS. With reference to the unassigned patient list 150, the main role of the reading room assistant is to assign exams to an available radiologist to be read. To do this, the reading room assistant clicks on the patient at the top of the list (to assure that cases are being read in order of acuity). Once clicked, a menu 154 is brought up that lists the available radiologists to perform the review. This list also includes a tab 156 in which the reading room assistant can add or delete a radiologist to the availability list. The unassigned patient list table includes a patient name column 158, a study type column 160, a site column (the site where the patient was imaged by the technologist, such as at one of the outpatient centers)

162, the patient waiting column 164, an estimated time to report column 166, and a requesting MD column 168.

The algorithm for estimating the time to report considers the average time to report for prior cases (preferably a rolling average to account for changing conditions/staff), how many radiologists are on the list, how urgent the case is versus other cases and may add a slush time (e.g. 10 minutes). The estimated time to report is updated/re-calculated periodically (e.g. every five minutes) to account for circumstances such as the addition of several high acuity patients into the list, which may cause a lower acuity patient's wait time to increase. More specifically, in an exemplary embodiment, the algorithm is as follows:

1. The following pieces of information are needed to track for a rolling duration:
   A. $TE_j$=The time that exam j enters the queue (i.e., end of procedure for exam j)
   B. $R_j$=The rank at which exam j enters the queue based on its urgency score
   C. $TL_j$=The time that exam j leaves the queue (i.e., is accepted by a radiologist)
2. Calculate the "velocity" for each exam that has exited the queue: $V_j=(TL_j-TE_j)/R_j$
3. Next, calculate the average velocity ($AV_b$) of all exams in each block b of rank positions:
   To calculate $AV_1$ (for R=1 through 5), sum up the $V_j$'s for all exams exiting the queue in the past 2 hours (the rolling duration) that entered in ranks 1-5 and divide that sum by the number of exams exiting the queue in the past 2 hours that entered in ranks 1-5
   Repeat this calculation for $AV_2$ (R=6 though 10), for $AV_3$ (R=11 though 15), and for $AV_4$ (R>15)
4. To estimate the time remaining before exam j will be read and dictated by a radiologist ($TR_j$) based on the exam's current rank in the queue ($R_t$) calculate:

---

If $R_t < 6$, then $TR_j = (R_t * AV_1) + 5$
If $5 < R_t < 11$, then $TR_j = (R_t * AV_2) + 5$
If $10 < R_t < 16$, then $TR_j = (R_t * AV_3) + 5$
If $15 < R_t$, then $TR_j = (R_t * AV_3) + 5$

---

5. To calculate the "expected time remaining" value that can be presented to patients, round $TR_j$ up to the next 10 minutes. For example, a patient with an exam having a calculated TRj of under 10 minutes would be told "less than 10 minutes," a patient with an exam having a calculated TRj of 10-20 minutes would be told "less than 20 minutes," and so on.

In another exemplary embodiment, the time-remaining algorithm was adjusted as follows:

1. The following pieces of information are needed to track for a rolling duration:
   A. $TE_j$=The time that exam j enters the worklist (i.e., end of procedure for exam j); defined as: max {time exam entered in ARTS, time exam completed in RIS}
   B. $R_j$=The rank at which exam j enters the worklist based on its urgency score
   C. $TL_j$=The time that exam j leaves the worklist (i.e., is dictated by a radiologist)
2. Calculate the "velocity" for each exam that has exited the worklist:

$V_j=(TL_j-TE_j)/R_j$

3. Next, calculate the average velocity (AV) of all exams:
   To calculate AV, sum up the $V_j$'s for all exams exiting the queue in the past 2 hours (the rolling duration) and divide that sum by the number of exams exiting the queue in the past 2 hours
4. To estimate the time remaining ($TR_{jt}$) before exam j will be read (between now, time t, and when the exam results will be available) based on exam j's current rank in the queue ($R_{jt}$), calculate: $TR_{jt}=(R_{jt}*AV)$
5. To calculate the "expected time remaining" value that can be presented to patients, round $TR_{jt}$ up to the next 10 minutes. For example, a patient with an exam having a calculated $TR_{jt}$ of under 10 minutes would be told "less than 10 minutes," a patient with an exam having a calculated $TR_{jt}$ of 10-20 minutes would be told "less than 20 minutes," and so on.

Once the patient is assigned to a radiologist, the patient's entry is removed from the list 150 and the reading room assistant can then refer the next patient on the list (which will then be on the top of the list).

Figure 8:
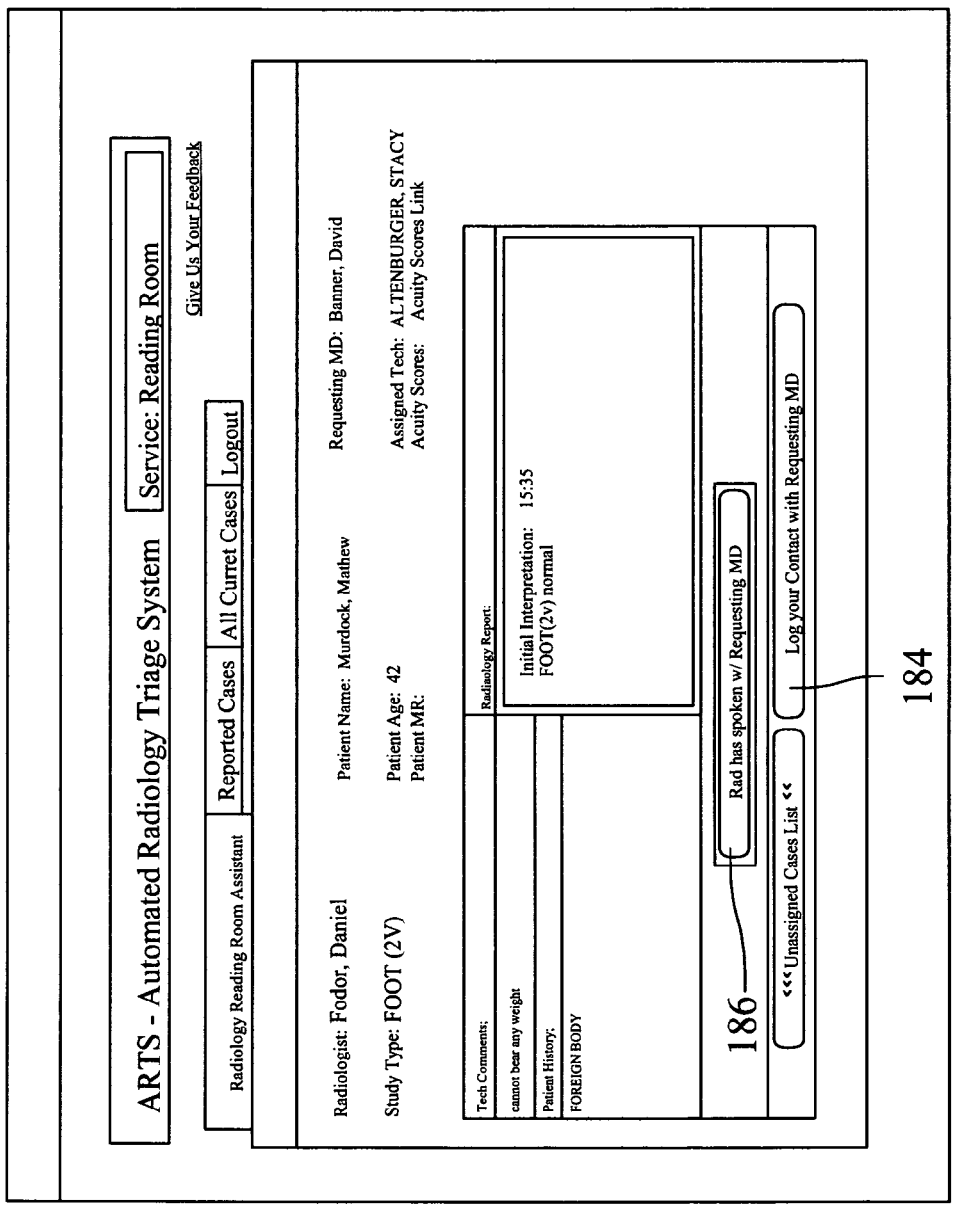
FIG. 8 is an exemplary screen shot of a "examination information" object operating on the reading room assistant's workstation.

The patient cases passed back from PPL list 152 includes a patient name column 170, a study type column 172, a status column 174, a time case entered column 176, an actual time reported column 178, an assigned technologist column 180, and the requesting MD column 182. When a case is passed back from PPL, the reading room assistant will click on the name on the list to complete the study. This will bring up the "view case details" screen, as shown in FIG. 8, which will include patient information, assigned technician information, requesting MD information, technologist's comments, patient history, and the radiology report. After the radiologist has spoken with the referring physician, the reading room assistant clicks on the button 184 to document such communications using the "add MD contact record" object 148. This process is especially useful if the radiology results have not yet been conveyed and it is desired to keep the exam on the list and document each contact with the doctor's office. This case will remain on the unassigned cases list until it is completed. If contact with the referring physician is complete and the report has been conveyed, the reading room assistant will then click on the button 186 right after, the system will automatically return to the work list page and this case will have been removed.

The radiologist's desktop will include a "view all current cases" object 188 a "view case" object 190, an "assign patient case" object 192, an "un-assign patient case" object 194, a "report case" object 196, a "view reported cases" object 198, an "add addendum" object 200, and an "add MD contact record" object 202 (See FIG. 2).

As shown in FIG. 9, the radiologist desktop operating the "view all current cases" object 188 will provide an assigned patient case list 204, which lists the cases that have been assigned to the individual radiologist. The assigned patient case list will include an "un-assign case" activation button in a separate column 208, will include a radiologist's name column 210, a patient name column 212, a study type column 214, a requesting MD column 216, a site column 218, an estimated time to report column 220, and a routing column 222. When the radiologist wishes to enter a report, the radiologist will first click on the patient's name in column 212. This will bring up the "report case" object 196, an exemplary screen of which is shown in FIG. 10.

Figure 10:
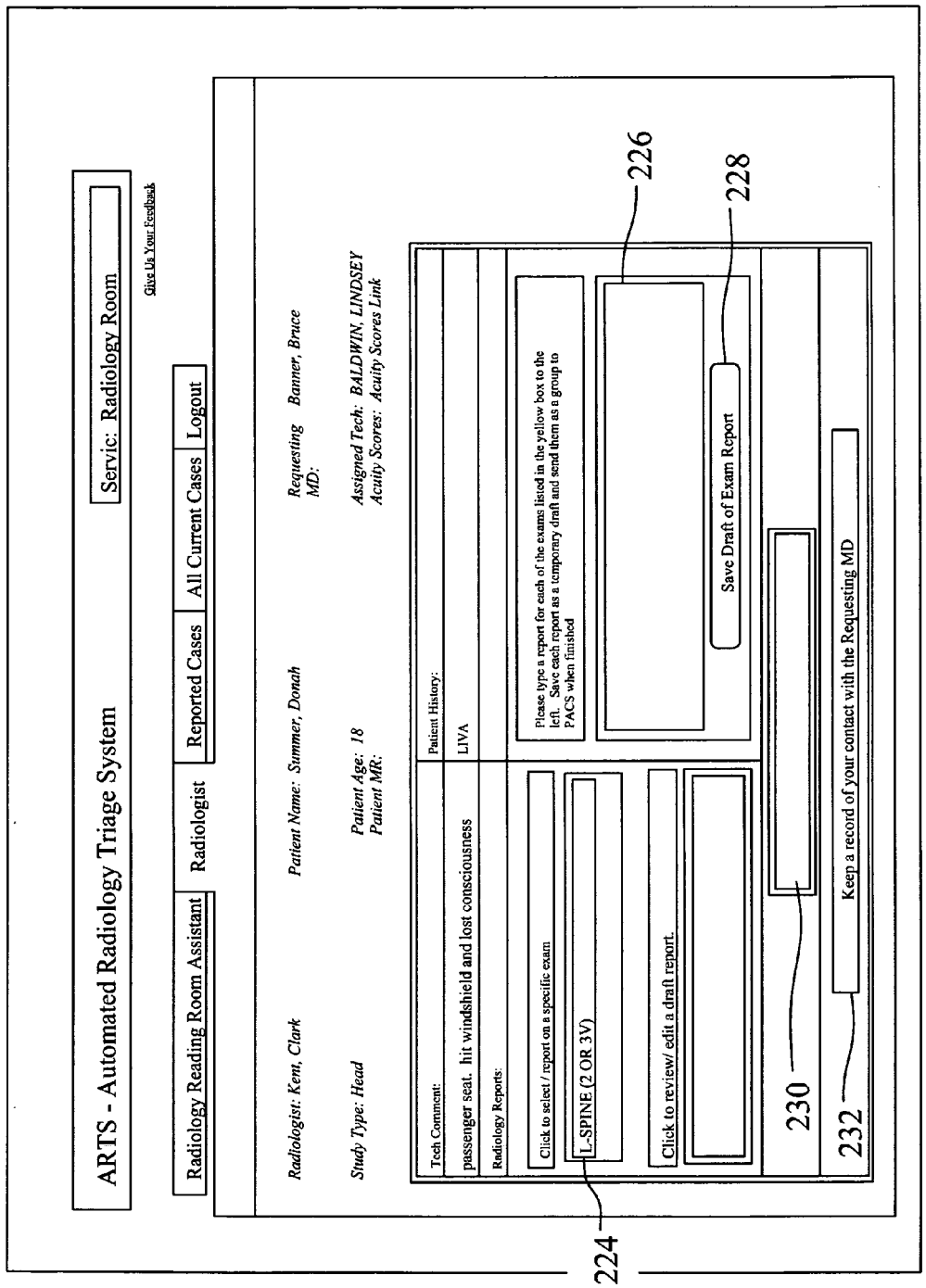
FIG. 10 is an exemplary screen shot of a "report case" object operating on a radiologist's workstation.
Figure 13:
FIG. 13 is an exemplary screen shot of a "contact record" object operating on a radiologist's workstation.

The "report case" screen of FIG. 10 shows patient demographic data and exam data captured from an associated patient database(s). The screen also shows technologist's comments, patient history, and any radiology reports that have already been entered. To enter or add to a report, the radiologist clicks on the exam in box 224 and the exam will then appear in box 226 followed by a colon. In this box 226 after the colon, the radiologist will type in his or her report, or utilize the available voice-recognition software to dictate a report. For multiple reports, the radiologist will click on the "save draft" button 228 for each examination. When all report drafts are saved, the radiologist will then click on the "send all reports to PACS" button 230. Upon clicking button, the report (1) is available in ARTS or PACS for in-house doctors; and (2) is sent to the PPL for contact with outside referring doctors (in embodiments where the ARTS system stands alone or is integrated with the PACS system, the button 230 may simply read "store report" or something similar). If the radiologist wishes to keep a record of contact with the referring MD, the radiologist will click button 232.

Figure 11:
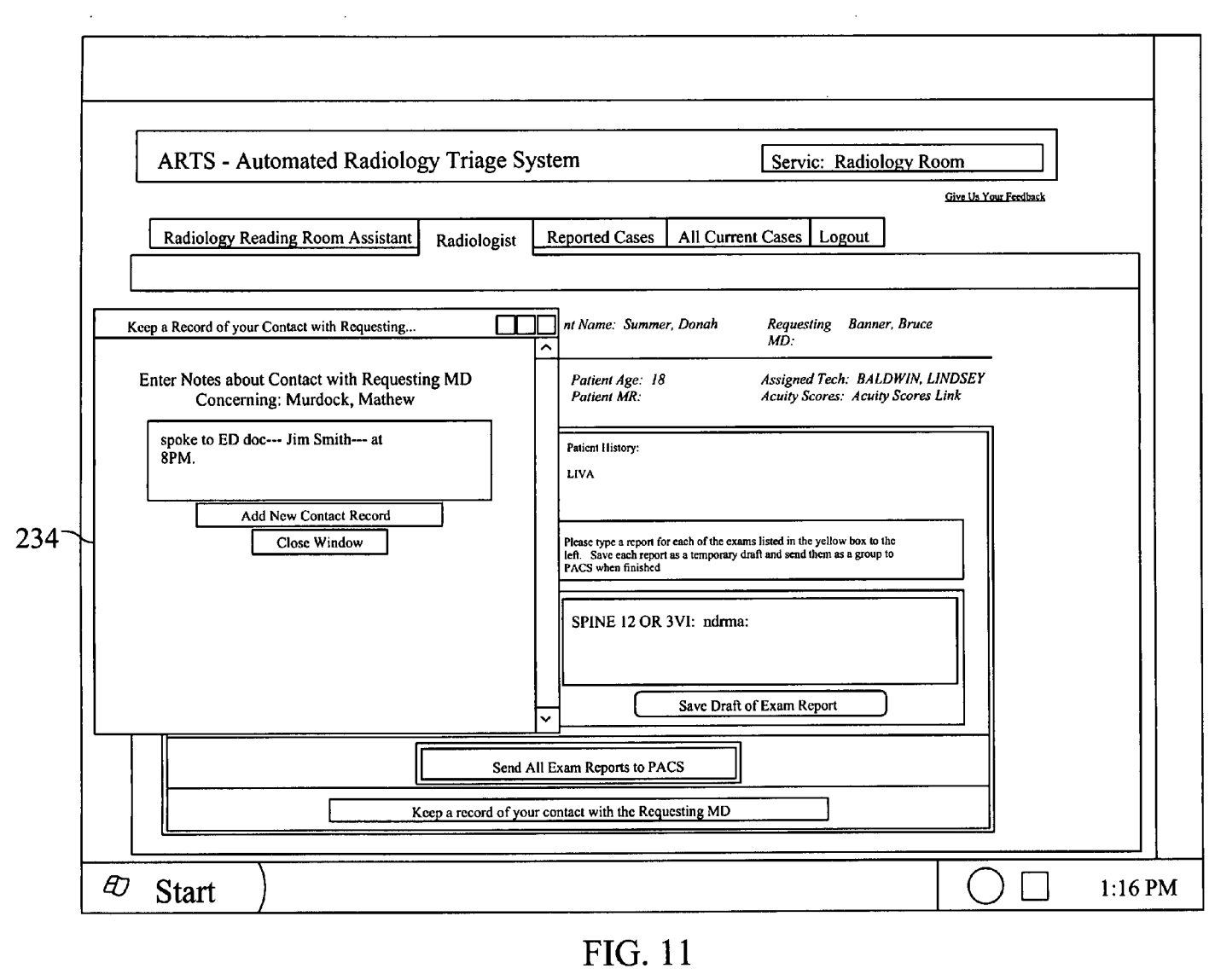

As shown in FIGS. 10 and 11, button 232 will activate "add MD contact record" object 148, which will bring up a window 234 that allows the radiologist to enter a contact record. If others have previously entered contact information (i.e. PPL or reading room assistant), it will appear here with a time stamp for when the contact occurred. This is a permanent record and can be accessed after the fact for information about what communication occurred with the case. Once the radiologist clicks on the "send all reports to PACS" button 230 the patient's name will be taken off the assigned patient case list 204 (in embodiments where the ARTS system stands alone or is integrated with the PACS system, the button 230 may simply read "store report" or something similar).

Figure 14:
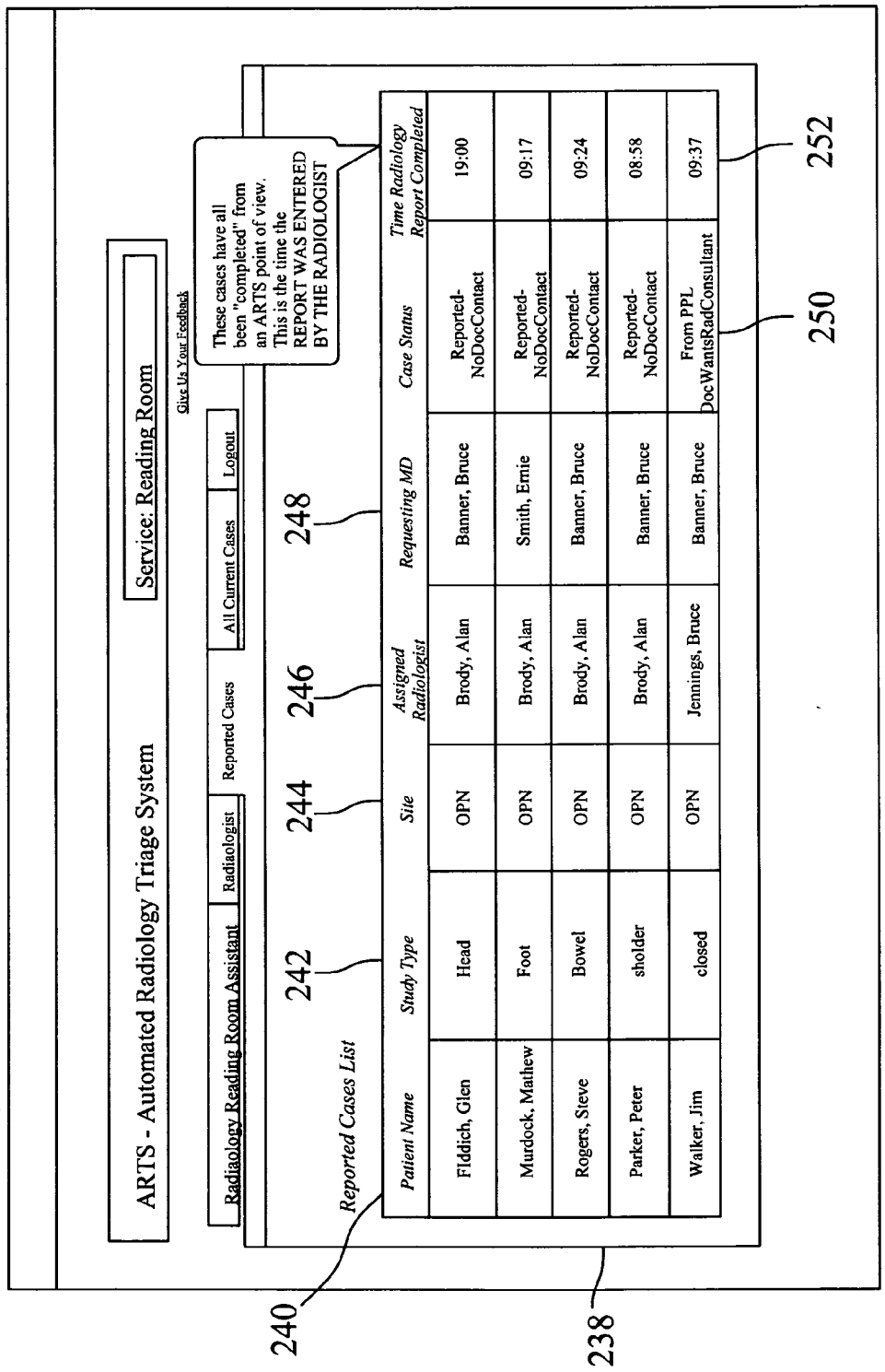
FIG. 14 is an exemplary screen shot of a "view reported cases" object operating on the radiologist's workstation.
Figure 15:
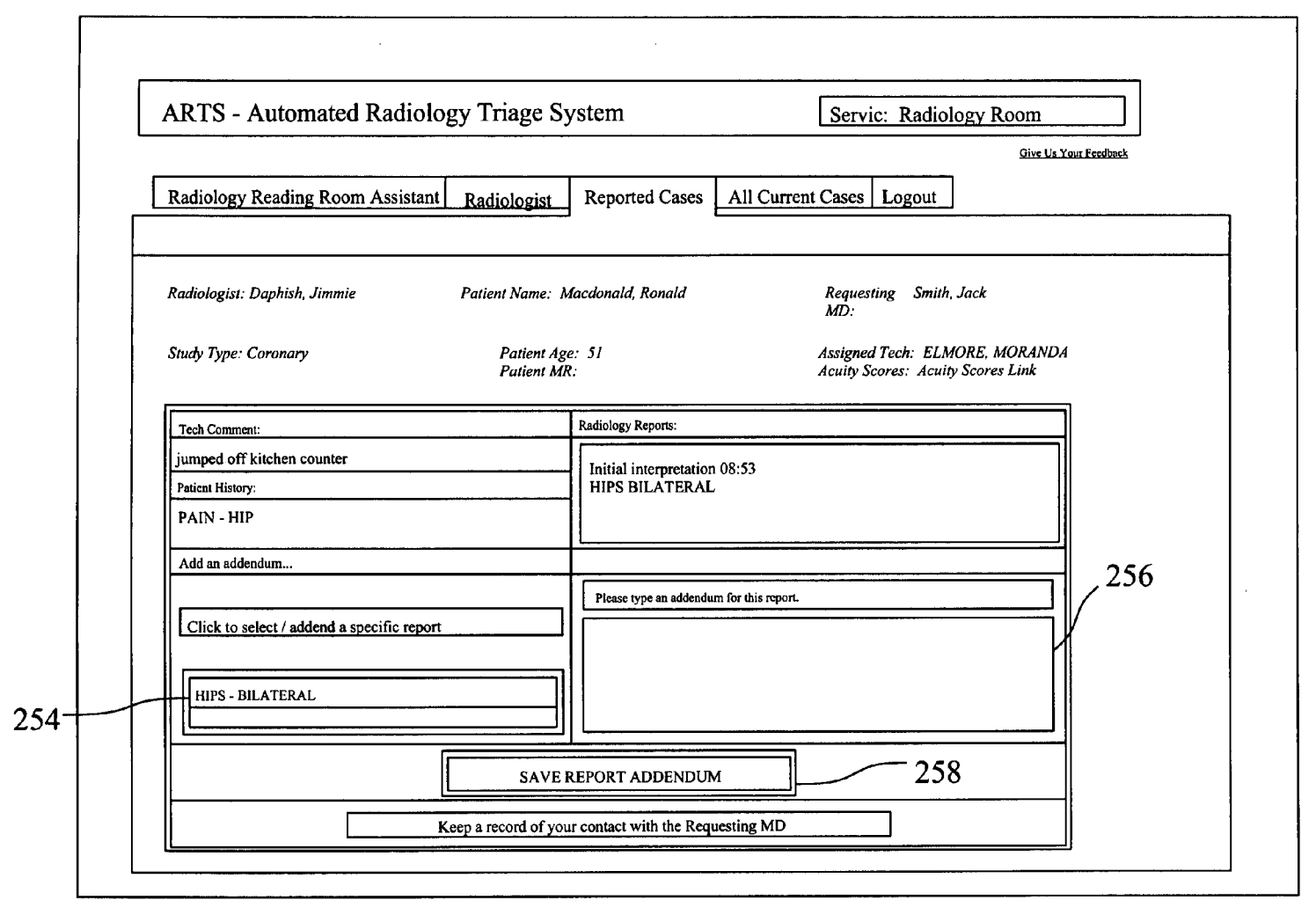

Referring again to FIG. 10, if the radiologist wishes to review again a reported case, the radiologist will click on the reported cases tab or icon 234 which will activate the "view reported cases" object 198, bringing up a screen such as shown in FIG. 14. This screen will provide a list of cases recently reported by the radiologist 238. For each entry in the list 238, a patient name column 240 will be provided with a study type column 242, a site column 244, an assigned radiologist column 246, a requesting MD column 248, a case status column 250 (indicating that the case has been reported and whether or not MD contact has been made), and a time that the radiology report was completed column 252. To add an addendum to report, the radiologist will click on the patient's name in the patient name column 240. This will bring up the "view reported cases" object 198 and open the examination as shown in FIG. 15.

To add an addendum to a reported case, the radiologist will click on the exam 254 and will then enter the addendum in box 256. When the "save report addendum" button 258 is activated the addendum will be sent to PACS and added to the preliminary report. The exam will also be sent back to the PPL work list for the referring MD to be re-contacted with this additional information (in embodiments where the ARTS system stands alone or is integrated with the PACS system, the button 258 may simply read "store report addendum" or something similar).

Referring back to FIG. 2, the PPL operator desktop 52 will include a "view current cases" object 260 that leads to "view case details" object 262, a "PPL work list pass back list" object 264 and an "add MD contact report" object 266. The primary purpose of the PPL operator desktop 52 is for the PPL operator to communicate reported cases to referring MDs (via telephone or other type of communication) and then to log PPL work list cases to the communication log, if necessary upon MD communication. The "MD contact record" object 266 is similar to the same-named objects in the other desktops and is provided to keep an accurate record of communications between the various parties involved in the examinations.

The front desk desktop 54 in the exemplary embodiment only includes a "view all current cases" object 268 and a "view details" object 270. This is the desktop viewable by a receptionist in a waiting room so that he or she can provide information to the waiting patients regarding the status of their examination, for example, how much time remains before the case is examined. It is also within the scope of the invention that the priority list may be displayed on a screen viewable by all patients sitting in a waiting area so they can monitor in real time the priority and time remaining in their examination, thus reducing a stress for the patients involved and also reducing the amount of interruptions that the patients might cause for various parties working at the location. It is preferred that such patient-viewable listings are codified (where each patient will know his/her code but not that of other patients) to protect the patients' confidentiality.

The prioritization algorithm uses the acuity scores entered by the technologist (or any other suitable person) as discussed above, and prioritizes each patient based upon an acuity algorithm. In the exemplary embodiment, the acuity algorithm is developed primarily upon mental heuristics of actual radiologists and physicians working in the field. In the exemplary embodiment, actual radiologists were asked to evaluate sets of over 500 hypothetical cases providing urgency ratings and urgency rankings for each of the cases. From these results, a second group comprising five of the most consistent radiologists were identified and used for further analysis and algorithm validation. Also, from the initial results, a variable compression scheme was used to simplify the algorithm. For example, with the exam type, 20 categories were reduced to 2; for medical acuity, 5 categories were reduced to 3; and for age, only 1 test was indicated (whether the patient was less than two years old or greater than two years old). Finally, a stepwise regression algorithm was used to provide variable beta weights while maximizing explained variance.

An example of the initial worksheets assessed by the radiologists is provided in FIG. 16. Two columns were provided, a left column in which the radiologist was to enter an urgency score (1=no urgency while 100=extreme urgency) and the right column was used to rank the five most urgent cases. By analyzing the results of this initial worksheet, an alpha version of the prioritization algorithm was produced. This algorithm was then tuned by applying the algorithm to additional hypothetical case studies and requesting the second group of selected radiologists to review the results from the initial algorithm. In the worksheet shown in FIG. 16, "type" is a type of study requested (examples include skull, chest, finger, etc.); "subjective acuity" is the degree of patient discomfort or medical acuity based upon perception of the technician (for example, is the patient short of breath? Is the arm visibly bent? Is the patient clearly in significant pain?); "medical acuity" is the type of iatrogenic stimulus (what brought the patient to medical attention); "patient waiting" indicates whether the patient and/or the patient's family is currently waiting at the front desk for reading to be relayed to the referring MD; "patient anxiety" indicates the technologist's subjective assessment of the mental anxiety of the patient or parent, including worry about possible diagnosis, or need to leave the facility as soon as possible; and "MD anxiety" refers to the technologist's subjective assessment of the medical anxiety or concern of the referring MD about the particular case.

FIG. 17 is the table provided to the second group of radiologists showing the prioritization from the preliminary algorithm. This table was provided to the second group of radiologists to learn whether or not they agreed with the algorithm's assessment (it is not necessary that this second group of radiologists know that the prioritization was made by a computer). This second group of radiologists was then asked to first make any changes he or she would make in the initial prioritization and then provide a numerical rating of overall how well he or she thinks that the cases were ordered. In an exemplary embodiment, based upon the results of this process, the following triage algorithm equation was developed:

URGENCY = Equation 1

$12.31 * SUBJACU + 25.94 * PATWAIT + 15.98 * REFANX +$ $15.35 * PATANX + 28.45 * DUMTYPE +$ $9.70 * DUMYOUNG + STAT * STATTIMEFACTOR +$ $NONSTAT * NONSTATTIMEFACTOR$

Where:

---

SUBJACU (Subjective Acuity)
IF SUBJACU1='Extreme' THEN SUBJACU=3
IF SUBJACU1='Moderate' THEN SUBJACU=2
IF SUBJACU1='Mild' THEN SUBJACU=1
PATWAIT (Patient Waiting?)
IF PATWAIT1='Yes' THEN PATWAIT=1, OTHERWISE PATWAIT=0
REFANX (Referring MD Anxiety/Concern)
IF REFANX1='High' THEN REFANX=1, OTHERWISE REFANX=0
PATANX (Patient/Family Anxiety/Concern)
IF PATANX1='High' THEN PATANX=1, OTHERWISE PATANX=0
DUMTYPE
DUMTYPE = 1 IF TYPE1='Airway' OR IF TYPE1='CSpine'
DUMTYPE = 0 OTHERWISE
DUMYOUNG
IF AGE < 2 yrs THEN DUMYOUNG=1, OTHERWISE DUMYOUNG=0
STAT
IF EXAM IS A "STAT" EXAM THEN STAT=1, OTHERWISE STAT=0
NONSTAT
IF EXAM IS A "NONSTAT" EXAM THEN NONSTAT=1, OTHERWISE NONSTAT=0
STATTIMEFACTOR
STATTIMEFACTOR = (Minutes Since Exam Completed / 15)$^3$
NONSTATTIMEFACTOR
NONSTATTIMEFACTOR = (Hours Since Exam Completed / 5.5)$^3$

---

In another exemplary embodiment, based upon feedback from use of the system, the triage algorithm equation was revised as follows:

URGENCY = Equation 2

$12.31 * SUBJACU + 25.94 * PATWAIT + 15.98 * REFANX +$ $15.35 * PATANX + 28.45 * DUMTYPE +$ $9.70 * DUMYOUNG + STAT * STATTIMEFACTOR +$ $(1 - STAT) * NONSTATTIMEFACTOR +$ $CALLREQUEST * STATTIMEFACTOR * 0.5$

Where:

---

SUBJACU (Subjective Acuity)
IF SUBJACU1='Extreme' THEN SUBJACU=3
IF SUBJACU1='Moderate' THEN SUBJACU=2
IF SUBJACU1='Mild' THEN SUBJACU=1
PATWAIT (Patient Waiting?)
IF PATWAIT1='Yes' THEN PATWAIT=1, OTHERWISE PATWAIT=0
REFANX (Referring MD Anxiety/Concern)
IF REFANX1='High' THEN REFANX=1, OTHERWISE REFANX=0
PATANX (Patient/Family Anxiety/Concern)
IF PATANX1='High' THEN PATANX=1, OTHERWISE PATANX=0
DUMTYPE
DUMTYPE = 1 IF TYPE1='Airway' OR IF TYPE1='CSpine'
DUMTYPE = 0 OTHERWISE
DUMYOUNG
IF AGE < 2 yrs THEN DUMYOUNG=1, OTHERWISE DUMYOUNG=0
STAT
IF EXAM IS A "STAT" EXAM THEN STAT=1, OTHERWISE STAT=0
NONSTAT
IF EXAM IS A "NONSTAT" EXAM THEN NONSTAT=1, OTHERWISE NONSTAT=0
STATTIMEFACTOR
STATTIMEFACTOR = MAXADDSTAT * EXP[−.693*((60/M)$^2$)], where
    MAXADDSTAT = a scaling factor establishing the waiting time's maximum contribution to the exam acuity score (initially set at 250),
        M = Minutes since exam completed
        EXP is the mathematical operand (e, the base of natural logarithms, raised to the power of)
NONSTATTIMEFACTOR
NONSTATTIMEFACTOR = MAXADDNONSTAT * EXP[−.1*((60/H)$^2$)], where
    MAXADDNONSTAT = a scaling factor establishing the waiting time's maximum contribution to the exam acuity score (initially set at 20),
        H = Hours since exam completed
        EXP is the mathematical operand (e, the base of natural logarithms, raised to the power of)
CALLREQUEST
CALLREQUEST = 1 if referring doctor requests to be contacted when dictation is complete, otherwise CALLREQUEST = 0

---

Following from the above invention summaries, it should be apparent to those of ordinary skill in the art that the present invention is not necessarily limited to health care applications, but may be applied to any business that provides customer service in an asynchronous model in which operational and psychological factors should be taken into account to prioritize workflow. For example, in an alternative exemplary embodiment, the present automated system and method for prioritization is applied to the automotive service industry. In this embodiment, the invention may be utilized by automotive service facilities that employ an appointment-scheduling software tool residing on a central server, which may be accessed by one or more workstations operatively coupled to the central computer through a direct connection or a network connection (wired or wireless). The system could operate, for example, on a Web-based client server model. Companies, professionals, diagnostic and repair personnel could license or subscribe to the system. The software could run locally, or nationally via remote servers.

This alternative embodiment of the present invention would provide an algorithm, similar to the algorithm of the first exemplary embodiment that would prioritize customers by taking into account factors such as availability of mechanics and lifts, whether a customer is waiting, whether the customer is anxious to leave, the predicted length of time the repair will take, periodic updates taking into account new information discovered during the course of the repair (for instance, additional unexpected repairs that also must be made), and the like. The system could also feature advanced filters and searching capabilities, to help users track workflow and specific cases transparently and easily.

Similar to the first exemplary embodiment, this alternate system could also support communication with customers, brokered by one or more telephone operators, who could be located distant from the repair facility. The operators, who would have real-time access to the system, as previously described, would convey information about the repair including what was done, the cost, projected time of completion, whether the repair is completed, and the like. If the customer requested a conversation with the mechanic or service manager directly, the operator cold connect the parties. If requested by the repair facility client, the operator could document such conveyances conveniently, in a permanent log provided by the software. If customers had useful further information to provide to service personnel, the operator could use the software to convey the information directly to the mechanic electronically, without interrupting his or her workflow.

Further, in this alternate embodiment, the system could allow customers to access a read-only portal, so that, for instance, they could keep track of their car's progress. This would help them to predict when the repair would be completed and the automobile available for pickup. Such a feature would also reduce the number of interrupting phone calls coming into the service department—a potential cost savings due to reduced staffing needs.

The alternate system could also incorporate the scheduling of future repairs, based on recommended service intervals and specific prior visits by customers. The system could broker e-mail, U.S. Post, or telephone reminders of such future visits.

Following from the above description and invention summaries, it should be apparent to those of ordinary skill in the art that, while the systems and processes herein described constitute exemplary embodiments of the present invention, it is to be understood that the invention is not limited to these precise systems and processes and that changes may be made therein without departing from the scope of the invention as defined by the claims. Additionally, it is to be understood that the invention is defined by the claims and it is not intended that any limitations or elements describing the exemplary embodiments set forth herein are to be incorporated into the meaning of the claims unless such limitations or elements are explicitly listed in the claims. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A computerized method for automated prioritization of waiting patients, comprising the steps of:
   for a plurality of patients, gathering with the assistance of a computer at least one medical factor associated with each patient's medical condition taken from a group consisting of (a) a type of injury, (b) a symptom, (c) a condition of the patient, and (d) a demographic statistic of the patient;
   for the plurality of the patients, gathering with the assistance of a computer at least one subjective perception associated each patient's medical condition taken from a group consisting of (a) anxiety of the patient, (b) anxiety of the referring physician, (c) anxiety of the reviewing attendee, and (d) whether the referring physician ordered the case STAT;
   generating, by a software tool on a computer server, an acuity score for each of the plurality of patients based at least upon weights applied to the at least one medical factor and the at least one subjective perception respectively gathered for each of the plurality of patients; and
   ordering, in a prioritized list by the software tool on the computer server, the plurality of patients for at least one of (a) medical treatment and (b) medical assessment, based at least upon the respective acuity scores generated for each of the plurality of patients;
   wherein the prioritized list is organized from top to bottom based upon the acuity scores generated for each of the plurality of patients.

2. The computerized method of claim 1, further comprising the steps of:
   for a new patient, gathering with the assistance of a computer at least one medical factor associated with the new patient's medical condition taken from a group consisting of (a) a type of injury, (b) a symptom, (c) a condition of the new patient, and (d) a demographic statistic of the new patient;
   for the new patient, gathering with the assistance of a computer at least one subjective perception associated the new patient's medical condition taken from a group consisting of (a) anxiety of the new patient, (b) anxiety of the referring physician, (c) anxiety of the reviewing attendee and (d) whether the referring physician ordered the case STAT;
   generating, by the software tool on the computer sever, an acuity score for the new patient based at least upon weights applied to the at least one medical factor and the at least one subjective perception gathered for the new patient; and
   re-ordering, by the software tool on the computer server, the plurality of patients and the new patient for at least one of (a) medical treatment and (b) medical assessment, based at least upon the respective acuity scores generated for each of the plurality of patients and the new patient;
   wherein the re-ordered prioritized list is organized from top to bottom based upon the acuity scores generated for each of the plurality of patients and the new patient.

3. The computerized method of claim 1, further comprising the step of displaying the prioritized list to an individual associated with providing the at least one medical treatment or medical assessment.

4. The computerized method of claim 3, further comprising the step of indicating with the assistance of a computer, that a patient in the prioritized list has received the at least one medical treatment or medical assessment.

5. The computerized method of claim 4, further comprising the step of re-ordering, by the software tool on the computer server, the plurality of patients, less the indicated patient, for at least one of (a) medical treatment and (b) medical assessment, based at least upon the respective acuity scores generated for each of the plurality of patients, less the indicated patient.

6. The computerized method of claim 1, further comprising the step of displaying the prioritized list on a display viewable by at least one of the plurality of patients.

7. The computerized method of claim 6, wherein the display is viewable by an attendant situated within a waiting room.

8. The computerized method of claim 1, further comprising the step of:
   for the plurality of the patients, gathering with the assistance of a computer operational aspects including (a) whether the patient is waiting in a waiting area of a medical facility or not, and (b) waiting time of the patient;
   wherein the acuity score generated for each the plurality of patients is based at least upon weights applied to the at least one medical factor, the at least one subjective perception and the operational aspects gathered for each of the plurality of patients.

9. The method of claim 8, wherein the weights are based upon mental heuristics gathered from a plurality of experienced professionals who perform the at least one medical treatment or medical assessment.

10. The method of claim 9, wherein the software tool on the computer server generates a higher acuity score if the patient is waiting in the waiting area of the medical facility as opposed to if the patient is not waiting in the waiting area of the medical facility.

11. The method of claim 10, wherein the software tool on the computer server generates a higher acuity score if the gathered subjective perception of the patient's anxiety is relatively high as opposed to if the gathered subjective perception of the patient's anxiety is relatively low.

12. The method of claim 11, wherein the software tool on the computer server generates a higher acuity score if at least one of the gathered subjective perception of the anxiety of the referring physician, and gathered subjective perception of the anxiety of the reviewing attendee is high as opposed to if the respective at least one of the gathered subjective perception of the anxiety of the referring physician and the gathered subjective perception of the anxiety of the reviewing attendee is relatively low.

13. The method of claim 12, wherein the software tool on the computer server generates a more urgent acuity score depending upon a perceived severity of the type of injury.

14. The method of claim 10, wherein the software tool on the computer server generates a higher acuity score the longer the patient has been waiting in the waiting area of the medical facility.

15. The method of claim 14, wherein the acuity score becomes exponentially higher in relation to the amount of time the patient has been waiting in the waiting area of the medical facility.

16. The method of claim 9, wherein the software tool on the computer server generates a higher acuity score if the referring physician ordered the case STAT as opposed to if the referring physician did not order the case STAT.

17. The method of claim 16, wherein the acuity score is a function of a STAT time factor.

18. The method of claim 1, wherein the weights are based upon mental heuristics gathered from a plurality of experienced professionals who perform the at least one medical treatment or medical assessment.

19. The method of claim 1, further comprising the step of estimating an additional waiting time until the at least one of the (a) medical treatment and (b) medical assessment will occur for each of the plurality of patients.

20. The method of claim 19, wherein the step of estimating a the additional waiting time for each of the plurality of patients is based upon a consideration of: (i) an average medical treatment or medical assessment time for previous patients and (ii) a number of patients ahead of a given patient in the ordered plurality of patients.

21. The method of claim 20, wherein the average medical treatment or medical assessment time is a rolling average.

22. The computerized method of claim 21, further comprising the step of displaying the prioritized list of patients on a viewable display and including the estimated additional waiting time for each patient in the display.

23. The computerized method of claim 21, further comprising the step of communicating an estimated additional waiting time to a corresponding waiting patient.

24. The computerized method of claim 23, wherein the estimating and communicating steps are repeated periodically.

25. A computerized method for automated prioritization of waiting patients, comprising the steps of:
for a plurality of patients, gathering with the assistance of a computer at least one medical factor associated with each patient's medical condition taken from a group consisting of (a) a type of injury, (b) a symptom, (c) a condition of the patient, (d) a reason for seeking a medical treatment, and (e) a reason for seeking a medical assessment;
for the plurality of patients, gathering with the assistance of a computer at least one demographic item associated with each patient;
for the plurality of the patients, gathering with the assistance of a computer at least one operational aspect taken from a group consisting of (a) whether the patient is waiting or not, (b) waiting time of the patient, (c) medical treatment facilities availability, (d) medical treatment staff availability, (e) medical assessment facilities availability, and (f) medical assessment staff availability;
generating, by a software tool on a computer server, an acuity score for each of the plurality of patients based upon the at least one medical factor, the at least one demographic item and the at least one operational aspect respectively gathered for each of the plurality of patients; and
ordering, in a prioritized list by the software tool on the computer server, the plurality of patients for at least one of (a) medical treatment and (b) medical assessment, based at least upon the respective acuity score generated for each of the plurality of patients;
wherein the prioritized list is organized from top to bottom based upon the acuity score generated for each of the plurality of patients.

26. The method of claim 25, further comprising the step of:
for the plurality of the patients, gathering with the assistance of a computer at least one subjective perception associated each patient's medical condition taken from a group consisting of (a) anxiety of the patient, (b) anxiety of the referring physician, and (c) anxiety of the reviewing attendee;
wherein the acuity score is generated in the generating step based at least upon a combination of the at least one operational aspect, the at least one medical factor, the at least one demographic item and the at least one subjective perception gathered for each of the plurality of patients.

27. The method of claim 26, wherein:
the software tool on the computer server in the generating step applies weights to the at least one operational aspect, the at least one medical factor, the at least one demographic item and the at least one subjective perception; and
the weights are based upon mental heuristics gathered from a plurality of experienced professionals who perform the at least one medical treatment or medical assessment.

28. The method of claim 25, further comprising the step of:
for the plurality of the patients, gathering with the assistance of a computer whether the referring physician ordered the case STAT;
wherein the acuity score is further generated in the generating step based upon whether or not the referring physician ordered the case STAT for each of the plurality of patients.

29. The method of claim 25, wherein:
the operational aspect includes (b) the waiting time of the patient; and in the generating step, the acuity score is generated in exponential relation to the gathered waiting time of the patient.

30. The method of claim 25, wherein:
the operational aspect includes whether or not the patient is waiting in a waiting area of a medical facility for the at least one of (a) medical treatment and (b) medical assessment; and
the generating step generates a higher acuity score if the patient is waiting in the waiting area as opposed to if the patient is not waiting in the waiting area.

31. A computerized method for automated prioritization of waiting patients, comprising the steps of:
calculating, by a software tool on a computer server, an acuity score for each of a plurality of patients for at least one of (a) medical treatment and (b) medical assessment, based at least upon a combination of two or more of, (i) at least one operational aspect, (ii) at least one medical factor, (iii) at least one demographic item, and (iv) at least one subjective perception gathered for each of the plurality of patients; and
ordering the plurality of patients into a prioritized list that is organized from top to bottom based upon the acuity score generated for each of the plurality of patients;
in the calculating step, the software tool on the computer server applies weights to the two or more of, (i) the at least one operational aspect, (ii) the at least one medical factor, (iii) the at least one demographic item, and (iv) the at least one subjective perception gathered for each of the plurality of patients;
the weights being previously generated from a step of collecting mental heuristics of a plurality of experienced professionals who perform the at least one medical treatment or medical assessment and a step of calculating the weights based upon, at least in part, the collected mental heuristics;
the at least one operational aspect being taken from a group consisting of (a) whether the patient is waiting in a waiting area of a medical facility or not, (b) an updated waiting time of the patient, (c) medical treatment facilities availability, (d) medical treatment staff availability, (e) medical assessment facilities availability, and (f) medical assessment staff availability;
the at least one medical factor being condition taken from a group consisting of (a) a type of injury, (b) a symptom, (c) a condition of the patient, (d) a reason for seeking a medical treatment, and (e) a reason for seeking a medical assessment; and
the at least one subjective perception being taken from a group consisting of (a) anxiety of the patient, (b) anxiety of the referring physician, and (c) anxiety of the reviewing attendee.

32. The method of claim 31, wherein the step of collecting mental heuristics of a plurality of experienced professionals include the steps of:
providing to a first group of experienced medical professionals a form that includes a first plurality of test-cases; and
rating by each of the first group of experienced medical professionals each of the test-cases in the form, the rating being a numerical rating based upon a level of urgency perceived for each test-case.

33. The method of claim 32, wherein each test case in the first plurality of test-cases includes (i) at least one hypothetical indication of operational aspect, (ii) at least one hypothetical indication of a medical factor, (iii) at least one hypothetical demographic item, and (iv) at least one hypothetical indication of a subjective perception.

34. The method of claim 32, wherein each test case in the first plurality of test-cases includes (i) at least one hypothetical indication of operational aspect, (ii) at least one hypothetical indication of a medical factor, and (iii) at least one hypothetical indication of a subjective perception.

35. The method of claim 32, further comprising the steps of:
generating a test-set of weights from the numerical ratings provided by the first group of experienced professionals;
ordering a second plurality of hypothetical test-cases using the test-set of weights;
providing the ordered second plurality of hypothetical test-cases to a second group of experienced medical professionals for review by the second group of experienced medical professionals; and
from the results of the review by the second group of experienced medical professionals, generating the weights to be applied to the two or more of, (i) the at least one operational aspect, (ii) the at least one medical factor, (iii) the at least one demographic item, and (iv) the at least one subjective perception gathered for each of the plurality of patients.

36. The method of claim 35, wherein the step of, from the results of the review by the second group of experienced medical professionals, generating the weights to be applied to the two or more of, (i) the at least one operational aspect, (ii) the at least one medical factor, (iii) the at least one demographic item, and (iv) the at least one subjective perception gathered for each of the plurality of patients, further includes a step of:
generating, by each of the second group of medical professionals, a numerical ranking of the how well each of the medical professionals considered the ordered second plurality of hypothetical test-cases to be prioritized.

37. The method of claim 35, wherein the step of generating the weights includes a step of modifying the test-set of rates.

38. A method for processing radiology cases comprising the steps of:
providing a software tool on a computer server accessible by a plurality of workstations coupled to the computer server over a computer network, wherein the software tool has access to a plurality of radiology case files corresponding to a plurality of pending radiology cases, and wherein the plurality of radiology case files includes information sufficient for one or more radiologists to conduct radiological examinations on the plurality of pending radiology cases;
assigning, with the assistance of the software tool, one or more of the plurality of pending radiology cases to a first radiologist and one or more of the remaining plurality of pending radiology cases to a second radiologist;
accessing the software tool over the computer network by the first radiologist utilizing a first one of a plurality of workstations to view one or more radiology case files pertaining to a pending radiology case assigned to the first radiologist, and recording an examination of the pending radiology case assigned to the first radiologist in the software tool by the first radiologist utilizing the first one of the plurality of workstations;
removing, by the software tool, the pending radiology case assigned to the first radiologist from the plurality of pending radiology cases;
accessing the software tool over the computer network by the second radiologist utilizing a second one of a plurality of workstations to view one or more radiology case files pertaining to a pending radiology case assigned to the second radiologist, and recording an examination of the pending radiology case assigned to the second radiologist in the software tool by the second radiologist utilizing the second one of the plurality of workstations; and removing, by the software tool, the pending radiology case assigned to the second radiologist from the plurality of pending radiology cases.

39. The method of claim 38, further comprising the steps of:

communicating at least one of the recorded examinations recorded by at least one of the first and second radiologists to a referring physician; and storing a record of the communicating step, by or with the assistance of the software tool.

40. The method of claim 39, wherein the communicating step includes the step of accessing, with the assistance of the software tool and utilizing a third one of the plurality of workstations, the recorded examinations recorded by at least one of the first and second radiologists by a communication assistant responsible for communicating data from the recorded examinations to the referring physician; and the step of storing a record of the communication step includes a step of recording by the communication assistant, with the assistance of the software tool and utilizing the third one of the plurality of workstations, a record of communications with the referring physician.

41. The method of claim 38, wherein the assigning step includes a step of accessing, with the assistance of the software tool and utilizing a third one of the plurality of workstations, a graphical user interface that provides list of the plurality of pending radiology cases by an third individual, and utilizing the graphical user interface to assign from the list one or more of the plurality of pending radiology cases to a first radiologist and one or more of the remaining plurality of pending radiology cases to a second radiologist.

42. The method of claim 41, wherein the list is ordered on the graphical user interface, from top to bottom, according to an acuity algorithm output.

43. The method of claim 38, wherein the assigning step includes a step of accessing, with the assistance of the software tool and utilizing one of the plurality of workstations, a graphical user interface that provides list of the plurality of pending radiology cases by the first radiologist, and utilizing the graphical user interface to assign from the list one or more of the plurality of pending radiology cases to the first radiologist.

44. The method of claim 43, wherein the list is ordered on the graphical user interface, from top to bottom, according to an acuity algorithm output.

45. The method of claim 38, wherein the assigning step includes a step of providing a graphical user interface by the software tool that provides a prioritized list of the plurality of pending radiology cases.

46. The method of claim 45, wherein:

the prioritized list is generated by the software tool utilizing an acuity algorithm that calculates priority based at least upon a combination of least one medical factor and at least one subjective perception gathered for each of the plurality of pending radiology cases;

the at least one medical factor is taken from a group consisting of (a) a type of injury, (b) a symptom, (c) a condition of the patient, and (d) a demographic statistic of the patient; and the at least one subjective perception is taken from a group consisting of (a) anxiety of the patient, (b) anxiety of the referring physician, (c) anxiety of the reviewing attendee, and (d) whether the referring physician ordered the case STAT.

47. The method of claim 46, wherein the acuity algorithm further calculates priority based at least one operational aspect, the at least one operational aspect being taken from a group consisting of (a) whether the patient is waiting or not, (b) waiting time of the patient, (c) medical treatment facilities availability, (d) medical treatment staff availability, (e) medical assessment facilities availability, and (f) medical assessment staff availability.

48. The method of claim 45, wherein:

the prioritized list is generated by the software tool utilizing an acuity algorithm that calculates priority based at least upon one aspect gathered for each of the plurality of pending radiology cases; and the at least one aspect is taken from a group consisting of (a) whether the patient is waiting or not, (b) waiting time of the patient, and (c) whether the referring physician ordered the case STAT.

49. The method of claim 48, wherein the acuity algorithm calculates priority based at least upon a combination of (a) whether the patient is waiting or not, (b) waiting time of the patient, and (c) whether the referring physician ordered the case STAT.

* * * * *